US009811391B1

(12) United States Patent
Barrett et al.

(10) Patent No.: US 9,811,391 B1
(45) Date of Patent: Nov. 7, 2017

(54) LOAD BALANCING AND CONFLICT PROCESSING IN WORKFLOW WITH TASK DEPENDENCIES

(71) Applicants: Ryan Barrett, San Francisco, CA (US); Taylor Sittler, San Francisco, CA (US); Krishna Pant, San Jose, CA (US); Zhenghua Li, San Jose, CA (US)

(72) Inventors: Ryan Barrett, San Francisco, CA (US); Taylor Sittler, San Francisco, CA (US); Krishna Pant, San Jose, CA (US); Zhenghua Li, San Jose, CA (US)

(73) Assignee: COLOR GENOMICS, INC., Burlingame, CA (US)

(*) Notice: Subject to any disclaimer, the term of this patent is extended or adjusted under 35 U.S.C. 154(b) by 0 days.

(21) Appl. No.: 15/449,579

(22) Filed: Mar. 3, 2017

Related U.S. Application Data

(60) Provisional application No. 62/303,529, filed on Mar. 4, 2016.

(51) Int. Cl.
*G06F 19/24* (2011.01)
*G06F 19/22* (2011.01)
(Continued)

(52) U.S. Cl.
CPC ............. *G06F 9/52* (2013.01); *G06F 9/4881* (2013.01); *G06F 19/18* (2013.01); *G06F 19/22* (2013.01); *G06F 19/24* (2013.01)

(58) Field of Classification Search
CPC .... G06F 9/52; G06F 9/4881; G06F 17/30949; G06F 17/30312; G06F 17/30318;
(Continued)

(56) References Cited

U.S. PATENT DOCUMENTS

2004/0015310 A1\* 1/2004 Yuste ...................... G06F 19/24
702/80
2007/0076936 A1\* 4/2007 Li .......................... G06F 19/22
382/129
(Continued)

FOREIGN PATENT DOCUMENTS

DE         EP2759953      \* 1/2013  ............. G06F 19/28

*Primary Examiner* — Jeffrey A Burke
(74) *Attorney, Agent, or Firm* — Kilpatrick Townsend & Stockton LLP

(57) ABSTRACT

Embodiments in the disclosure are directed to the use of distributed computing to align reads against multiple portions of a reference dataset. Aligned portions of the reference dataset that correspond with an above-threshold alignment score can be assessed for the presence of sparse indicators that can be categorized and used to influence a determination of a state transition likelihood. Various tasks associated with the processing of reads (e.g., alignment, sparse indicator detection, and/or determination of a state transition likelihood) may be able to take advantage of parallel processing and can be distributed among the machines while considering the resource utilization of those machines. Different load-balancing mechanisms can be employed in order to achieve even resource utilization across the machines, and in some cases may involve assessing various processing characteristics that reflect a predicted resource expenditure and/or time profile for each task to be processed by a machine.

20 Claims, 16 Drawing Sheets

(51) Int. Cl.
*G06F 19/18* (2011.01)
*G06F 9/52* (2006.01)
*G06F 9/48* (2006.01)

(58) Field of Classification Search
CPC .......... G06F 19/10; G06F 19/22; G06F 19/18; G06F 19/24
See application file for complete search history.

(56) References Cited

U.S. PATENT DOCUMENTS

| | | | |
|---|---|---|---|
| 2008/0256070 A1* | 10/2008 | Inglis | G06F 19/28 |
| 2010/0100366 A1* | 4/2010 | Terai | G06F 19/24 703/11 |
| 2012/0023110 A1* | 1/2012 | Zidan | G06F 19/22 707/748 |
| 2014/0214579 A1* | 7/2014 | Shen | G06F 19/28 705/26.1 |
| 2015/0199473 A1* | 7/2015 | Kural | G06F 19/22 702/19 |
| 2015/0234981 A1* | 8/2015 | Naidich | G06F 19/22 506/8 |
| 2016/0171153 A1* | 6/2016 | Van Rooyen | G06F 19/22 702/20 |
| 2016/0180019 A1* | 6/2016 | Van Rooyen | G06F 19/24 702/19 |
| 2016/0292198 A1* | 10/2016 | Karten | G06F 17/30 |
| 2017/0068776 A1* | 3/2017 | Godinez-Moreno | G06F 19/12 |
| 2017/0169159 A1* | 6/2017 | Sazonov | G06F 19/18 |

\* cited by examiner

LOAD BALANCING AND CONFLICT PROCESSING IN WORKFLOW WITH TASK DEPENDENCIES

CROSS-REFERENCES TO RELATED APPLICATIONS

This application claims the benefit of and the priority to U.S. Provisional Application No. 62/303,529, filed on Mar. 4, 2016, which is hereby incorporated by reference in its entirety for all purposes.

FIELD

Methods and systems disclosed herein relate generally to the efficient distribution of computational tasks for the integration and analysis of data across a group of computing machines, and the processing of multi-alignment results for individual reads. In some cases, the computational tasks are not completely independent of one another and the inter-dependency of the computational tasks must be considered in balancing the resource usage of the group of computing machines.

BACKGROUND

Computational tasks in a workflow are often distributed among a plurality of computing machines in order to gain efficiency. However, this distribution of tasks can be problematic when the tasks are not completely independent of one another. This means that the tasks cannot simply be divided up and distributed to be performed in parallel. In some cases, the resulting outputs of tasks of a single type may need to be merged or combined in order to allow successive tasks in the workflow to be performed.

Furthermore, different types of tasks in the workflow may take up varying amount of computing resources. There may be even greater variation in the required amount of computing resources depending on the underlying data operated on in those tasks. The different machines may also have their own varying levels of resource utilization. All of these factors may make it difficult to distribute tasks among the plurality of computing machines in order to achieve even resource utilization across those machines.

Task processing can be further complicated when performance of a first task produces multiple, conflicting results. When a second task depends on a result of the first task, this can slow a workflow and/or hamper a quality and/or accuracy. For example, one potential response to detecting multiple, conflicting results is to trigger a task to re-verify input data for the first task. This approach then requires a verification task to be performed and potentially for the first task to be repeated before the second task can be performed, thereby introducing a delay. Another approach is to discard the results, though this approach can degrade a quality of a result produced by the second task.

There exists a need for techniques to allow for the processing of computational tasks in a workflow to be distributed across a plurality of computing machines in a manner that accounts for the type of task, the data operated on in those tasks, and the varying resource utilization of the machines. There is a further need for techniques to address conflicting results produced in early tasks in a workflow.

BRIEF SUMMARY

Some embodiments described herein relate to receiving reads in real-time and/or in a stream from a data generator system and processing each read upon receipt, prior to storage and/or prior to receiving all of the reads being generated at the data generator system (associated with particular client) via a particular processing of a corresponding sample.

In certain embodiments, a computer-implemented method is disclosed that involves receiving a plurality of reads, with each read in this plurality of reads being associated with a single client. An alignment process may be performed on each read in this plurality of reads. This alignment process may involve using a read and a reference dataset to generate an alignment result, with the alignment result identifying one or more portions of the reference data set to which the read is to be aligned. The reference dataset may include a vector of identifiers at a plurality of positions, such that at each position of the plurality of positions there is a reference data identifier corresponding to that position. The method may further involve identifying a first pre-identified portion of the reference dataset, with this first pre-identified portion being related to a second pre-identified portion of the reference data set. Both the first pre-identified portion and the second pre-identified portion may correspond to a subset of the plurality of positions in the reference dataset. For each position of one or more positions of the first pre-identified portion, a subset of the set of reads can be identified. Each read in this subset may have an identifier aligned to the position. For each of the one or more identifiers, a quantity of the subset of reads can be determined that includes the identifier at a read position aligned to the position. The method may further involve determining whether an downstream-processing criterion is satisfied based on the quantity of the subset of reads that includes the identifier at the read position aligned to the position. If that downstream-processing criterion is satisfied, it can be determined whether the identifier matches a reference-data identifier in the reference data set at the position. If the identifier does not match the reference-data identifier at the reference data set at the position, then a sparse indicator can be defined that represents a difference between the identifier and the reference-data identifier. That sparse indicator can be assigned to a bucket representative of a state-transition likelihood attributable to the sparse indicator. Furthermore, it can be determined whether a data verification condition is satisfied based on the bucket assignments of the various sparse indicators. Upon determining that the data verification condition is satisfied, a communication can be transmitted to a data generation system that identifies the client.

In some embodiments, the processing of reads (e.g., performing alignment, sparse indicator detection, and/or determination of a state transition likelihood) is distributed across machines. Such distribution can include using a task-distribution protocol that can be used to determine which machines are to perform which tasks. Each task may include processing a given individual read or collection thereof. For example, a first set of tasks may include aligning each of a first set of reads to a reference dataset. One approach is to distribute tasks based on a task number (e.g., such that each machine is assigned a similar number of tasks) or read sizes (e.g., such that, for a machine that is processing a larger read, a bias is implemented against assignment of other tasks). This approach may result in uneven resource usage and/or idle times. Another approach is to distribute tasks based on processing statuses and task completion. For example, a load-balancing machine may iteratively assign tasks to machine based on when tasks are reported being completed. Yet another approach is to use a predictive technique and/or an initial assessment to predict a processing time and/or resource expenditure that will be required for completion of each tasks, and tasks may be assigned in a prospective load-balancing manner. This type of parallel processing may be particularly useful if a large set of reads is to be re-processed based on identification of a new reference dataset or identification of a problem or potential improvement in an analysis pipeline. This type of parallel processing may also be useful if a new sparse indicator is classified, such that many clients' data can be quickly analyzed using this approach.

In some embodiments, a load-balancing technique for parallel processing can include generating a processing characteristic that reflects a predicted resource expenditure and/or time profile for each task to be processed by a machine. A load-balancing or scheduling machine may then assign tasks based on the processing characteristic to try to equilibrate machine loads (e.g., regarding required processing, memory, or bandwidth). This may require a pre-assessment that may perform an initial task to evaluate subsequent tasks (e.g., an initial pair-wise alignment to determine whether there is a perfect match, no match or multiple matches.) Alignment tasks may be have a shape defined based on how many potential alignment sites there are or may be sub-divided based on a number of potential alignments. Another approach is to redefine tasks to be of similar shape and to divide tasks based on number. This may reduce the need for a cluster management system.

In some embodiments, the use of parallel processing can provide the computational capability of aligning individual reads to multiple parts of a reference dataset. For example, different machines may assess a potential alignment of a read and a different part of a reference dataset. Intelligent processing may detect areas of the reference dataset that differ and focus machine division on those portions. For example, a multi-dimensional suffix tree may be used to identify potential portions of the reference dataset for alignment assessment.

In some embodiments, tasks for the detection of sparse indicators can be distributed across machines. This is particularly true if a sparse indicator is a certain type of sparse indicator (e.g., if a read differs by a reference database by more than a few units). Predicting and/or defining task shapes may be easier for tasks involving the detection of sparse indicators than alignment tasks, since a portion of a sequence is already known and an initial assessment can determine a degree which the read matches the corresponding reference-sequence. Sequence reads with weaker matches may be predicted to require more substantial resource utilization.

In some instances, reads are evaluated "horizontally", whereby each read is individually evaluated (e.g., to identify its alignment and/or detect sparse indicators). In some embodiments, a vertical analysis may be used (additionally or alternatively), whereby a given portion of a reference dataset may be identified (e.g., one that is associated with a newly classified sparse indicator), and all reads aligned with part or all of that portion can be identified. Potentially, an entire reference dataset may be analyzed via successive portions in this manner (e.g., to identify portions of high sparse indicator occurrence). This approach may involve a fuzzy, imprecise and/or flexible queries and repeated queries of a large data set. Thus, it may be well-suited for parallel processing.

BRIEF DESCRIPTION OF THE DRAWINGS

The present disclosure is described in conjunction with the appended figures.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart or diagram may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

Example Embodiments

Figure 1:
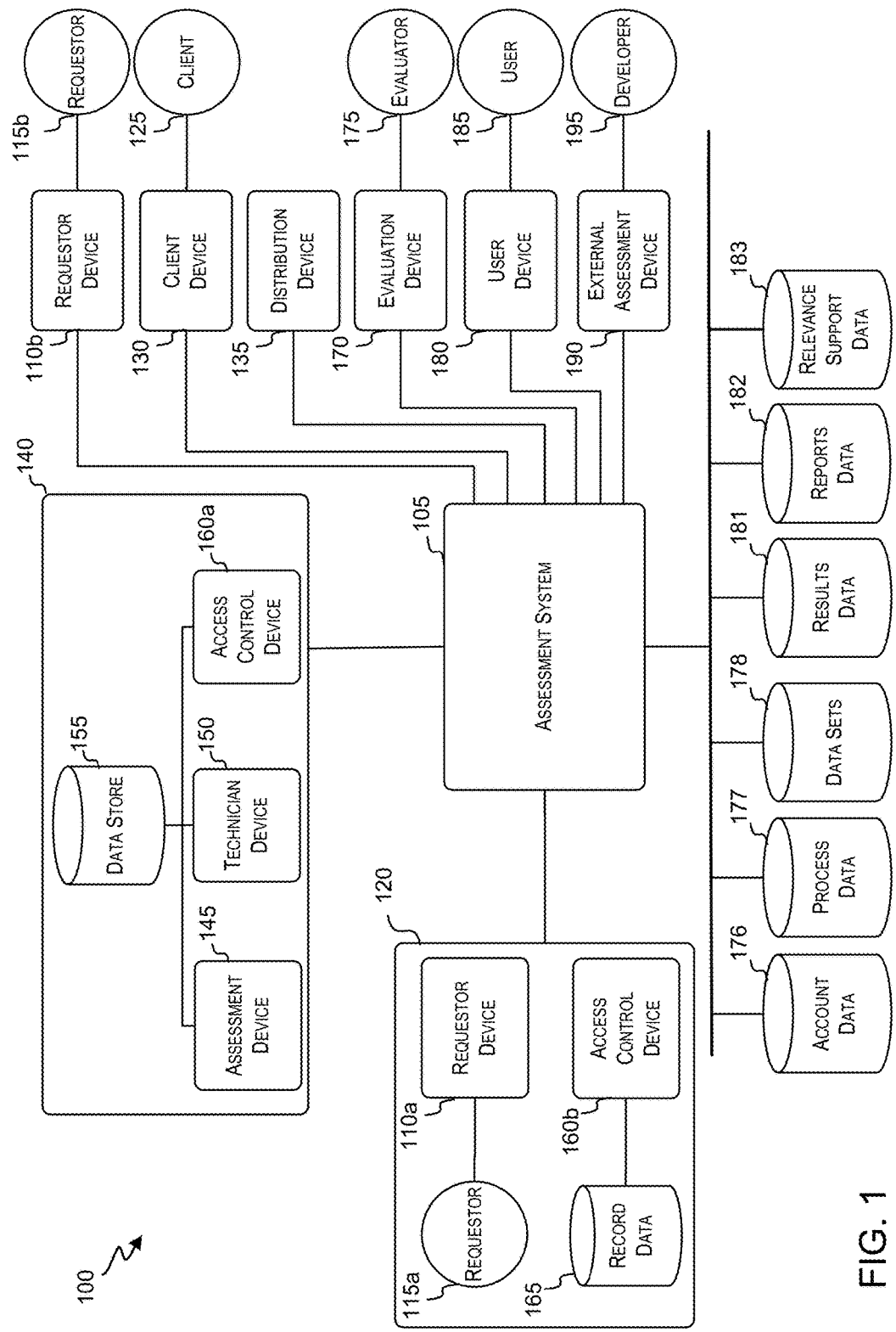
FIG. 1 shows a representation of a data processing network, in accordance with some embodiments of the invention.

With regards to the figures, FIG. 1 shows a representation of an assessment network 100, which may include any combination of the various systems or components shown. An overview of the interactions between the various components of assessment network 100 are described below.

In some embodiments, the assessment network 100 may include an assessment system 105 capable of receiving an electronic request from a requestor device 110. The assessment system 105 may include one or more electronic devices (e.g., storage devices, servers, and/or computers) and may, but not need, reside partly or entirely at a remote server. A requestor device 110 may be configured and located to receive input from a requestor 115. In some embodiments, a requestor device 110a is located in an external facility 120. In some embodiments, a requestor device 110b includes an internally linked requestor device 110b, such as one that itself receives invitations to generate electronic requests. The invitations received by the requestor device 110b may come from any source, including the assessment system 105.

The electronic request received by the assessment system 105 from the requestor device 110 may include instructions to conduct a data-set analysis, for example. Optionally, such an electronic request may be encrypted prior to transmission and decrypted upon receipt. In some embodiments, the electronic request may identify, or otherwise indicate, one or more states to be evaluated during the analysis and/or during an assessment. In some embodiments, the electronic request may identify a client and/or include additional data pertaining to the client, such as client-identifying data.

In some embodiments, the afforementioned client may be the client 125. In some embodiments, the client may be equated to, by the assessment system 105, a client device 130. In some instances, a client device 130, associated with the client 125, initially transmits a preliminary electronic request for the analysis and/or assessment to assessment system 105. For example, such a preliminary electronic request may be initiated via interaction with a website associated with the assessment system 105. The same or a subsequent preliminary request may identify a particular requestor (e.g., by name, office location, phone number, and/or email address) and/or may request that a requestor, such as a requestor 115b associated with an internally linked requestor device 110b, submit such a request.

When a particular entity is identified in a preliminary electronic request, the assessment system 105 may identify a destination address (e.g., IP address or email address) associated with the entity and transmit a communication identifying information associated with the preliminary request (e.g., the client, a type of analysis, and so on). The communication may include a partial instruction and/or an input field that would confirm that the request of the client 125 is to be generated and transmitted back to the assessment system 105. Such a communication may facilitate receipt of the electronic request from the requestor device 110b by the assessment system 105.

When it is requested that a requestor, such as a requestor 115b, associated with an internally linked requestor device 110b submit such a request, the assessment system 105 may transmit a similar communication to a requestor device 110b that may have been selected from among multiple internally linked requestor devices. The selection may be based on a load balancing technique, availability hours, expertise, locations of the multiple requestor devices, a pseudo-random selection technique, and/or an entity affiliation.

Once the electronic request has been received from a requestor device 110 (e.g., in response to a preliminary request from a client device 130) by the assessment system 105, the assessment system 105 may evaluate the request to ensure that all required data has been provided and that all required data pertaining to the client 125 has been identified (e.g., via the request, a preliminary request and/or stored data). If the assessment system 105 determines that all required information has not been identified, an additional request for missing information may be transmitted back to the requestor device 110 and/or the client device 130. In response, an updated electronic request with the updated information may be transmitted back to the assessment system 105. In various instances, an object provided to a user depends on an analysis requested, whether, and what kind of, new data-generation processing of a material is required for the analysis, a number of data-set units being assessed (e.g., and whether they have been previously assessed), a number and/or type of analyses being requested, a number and/or type of analyses previously requested, a number and/or type of analyses predicted to be requested subsequently, a state for which a progression prediction is being requested, whether a user is granting other entities' access to the client's data or results, whether a user is authorizing additional analyses to be performed on the client's data, and/or whether a user is granting permission to send offers to request user access to results or reports other than those initially being requested.

When all required information has been provided to the assessment system 105, the assessment system 105 may send an instruction communication to a distribution device 135. Optionally, that instruction communication may be encrypted prior to transmission; such an encrypted communication may be decrypted upon receipt. Optionally, that instruction communication may be transmitted over one or more network links, such as including transmission, at least in part, over a public communications network, such as the Internet. That instruction communication may include, for example, a name and address of the client 125 and, in some instances, an indication as to what is to be provided to the client 125 for collection of a material for subsequent analysis. For example, an initial electronic request received by the assessment system 105 may indicate a type of analysis that is to be performed on a material (e.g., an analysis pertaining to a likelihood of getting one or more particular types of states) and/or a type of material (e.g., type of sample) that is to be analyzed. This instruction communication sent by the assessment system 105 may identify the type of analysis, type of material, and/or kit associated with collection of the material. The instruction communication may thus facilitate and/or trigger a physical distribution of instructions, which may include a kit or other sample collection materials, to a client address. The instructions may include, for example, instructions as to how to collect a material, a container for storing the material and/or information pertaining to an instruction or type of analysis to be conducted. Alternatively, the instructions may be provided to a facility, such as the external facility 120 associated with a requestor 115a, that may aid client 125 in obtaining the material.

When the client 125 provides the material, the material may then be directed to and received at a data generator 140 in order for analysis to be performed. In some embodiments, the data generator 140 may be part of a facility. In some of such embodiments, the data generator 140 may include one or more assessment devices 145 configured to generate data reads, data elements, or data sets for various data-set units using the material received from the client 125. For example, in some embodiments the assessment device 145 may include a data-characterizer device (e.g., sequencer and/or polymerase chain reaction machine). Such a data-characterizer device can be used with the material received from the client 125 to generate a set of data reads.

In some embodiments, the data generator 140 may further include one or more technician devices 150, such as a desktop or laptop computer. In some embodiments, various components of the data generator 140 may be used to generate data. For example, data may be generated by one or more devices (e.g., one or more of the assessment device 145 and/or technician device 150). The generated data may be stored at a data store 155, which may be remote from all the data generator device or part of a data generator device. The data may, for example, include identifying client information (e.g., a name and address), facility information (e.g., location and name), device specifications (e.g., manufacturer and model of assessment device) and data. In some embodiments, a facility, such as external facility 120 or data generator 140, may correspond to a lab.

In some instances, data is optionally collected or requested from one or more external systems. Thus, assessment system 105 may transmit one or more other data requests and one or more other data transmissions may provide the other data. For example, one or more data sets and/or one or more processed versions thereof (e.g., identifying one or more sparse indicators) corresponding to an existing or new client may be received from an external system. As another example, the assessment system 105 may transmit a client data set to an external system, and the external system may then return a result of an assessment of the client data set. As yet another example, other data may include a data set (or results based on such data) corresponding to another individual (e.g., an entity related to a client and/or an entity sharing a characteristic with a client). The other individual may be, for example, identified based on input from the client and/or automatically identified (e.g., based on a query of a data store to identify clients associated with inputs or results indicating a shared characteristic or relationship). In some instances, a state assessment variable may be generated based on data from multiple other people, and the data for each other person may be weighted based on (for example) how closely related the person is with a client and/or how many or which characteristics the person shares with a client.

In some embodiments, the data generator 140 may include an access control device 160a which may control which devices and/or entities may gain access to the generated data. These access control restrictions may apply to devices and/or entities internal to the data generator 140 and/or to devices and/or entities external to the data generator 140. Access control device 160a may implement one or more rules, such as restricting access to client data to one or more particular devices (e.g., associated with assessment system 105). Such access may further or alternatively be controlled via logins, passwords, device identifier verification, etc.

In various instances, access control device 160a controls access via control of pushed transmissions and/or via control of processing pull requests. For example, a rule may indicate that data pertaining to a material, such as a sample, is to automatically be transmitted to a particular assessment system 105 (and/or device associated therewith) upon completion of a facility-based assessment or detection of particular data (e.g., data matching a request). Access control device 160a may then monitor for such a criterion to be met and may then generate and transmit appropriate data.

The generated data may include a plurality of data reads, data elements, or sets (e.g., each data read in the plurality of data reads corresponding to a same client, or at least some of the plurality of data reads corresponding to different clients). In various instances, the data may be transmitted to the assessment system 105 in a batch-mode, in a streaming mode, in real-time as data is produced, and/or upon request. The data may also be stored at a data store local or remote to the data generator 140. A given transmission or stream may include data that corresponds to a single, or in other instances to multiple, client, sample, and/or data reads. In some instances, the access control device 160a evaluates one or more transmission conditions, which may indicate, for example, whether and/or what data is to be transmitted given a quantity of data collected, (e.g., generally, since a past transmission and/or for a given client or sample) and/or given a time since a previous transmission. In one instance, as data reads are generated by an assessment device, a data set is generated so as to include each new data read and one or more identifiers (e.g., of a client, sample, time and/or facility device). The data may then be transmitted via a discrete communication (e.g., via FTP, over a webpage upload, email message, or SMS message) to assessment system 105. In one instance, the data may then be appended to a stream that is being fed to the assessment system 105.

It will be appreciated that the assessment network 100 may, in some instances, include multiple data generators 140, each of which may include any combination of an assessment device 145, technician device 150 and/or access control device 160a. Further, a given data generator 140 may, in some instances, include multiple assessment devices 145, multiple technician devices 150 and/or multiple access control devices 160a. Thus, data received at assessment system 105 may include data collected by and/or derived from data collected by different assessment devices, which may result in the data having different biases, units, and/or representation. Similarly, personnel operating different technician devices 150 may utilize different protocols and/or data interpretation techniques, which may again result in receipt of data at assessment system 105 that has different biases, units, variables, and so on. Further, even data originating from a same device may, in time, exhibit different biases, units, and so on, which may be a result of a manipulation of a control of the device and/or equipment wear.

Thus, in some instances, the assessment system 105 performs a comparison across data received from a data generator device (e.g., an access control device 160*a* or directly from an assessment device 145 or technician device 150) associated with data generator 140. The comparison may be across, for example, data collected at different facilities, data based on measurements collected at different devices, and/or data collected at different times. In some embodiments, the assessment system 105 performs a comparison across data received from different devices, such as devices associated with multiple data generators 140. It will be appreciated that the comparison may include a direct comparison of collected data or comparing preprocessed versions of the collected data. For example, received data may first be preprocessed via a transformation and/or dimensionality-reduction technique, such as principal component analysis, independent component analysis, or canonical correspondence analysis.

The comparison may include, for example, performing a clustering technique so as to detect whether data corresponding to a given facility, device, or time period predominately resides in a different cluster than data corresponding to one or more other facilities, devices, or time periods. The clustering technique may include, for example, a connectivity based clustering technique, a centroid-based clustering technique (e.g., such as one using k-means clustering), a distribution-based clustering technique, or a density-based clustering technique.

The comparison may additionally or alternatively include a statistical technique, such as one that employs a statistical test to determine whether two or more data sets (e.g., corresponding to different facilities, devices, or time periods) are statistically different. For example, a Chi-square, t-test or ANOVA may be used.

The comparison may additionally or alternatively include a time-series analysis. For example, a regression technique may be used to determine whether output from a given device is gradually changing in time.

When it is determined that particular data corresponding to a given facility, device, or time period is different than data corresponding to one or more other facilities, devices, or time periods (e.g., is assigned to a different cluster than other data or is associated with a p-value below a threshold), a normalization and/or conversion factor may further be identified. For example, a normalization and/or conversion factor may be identified based on centroids of data clusters and/or inter-cluster distances. As another example, a linear or non-linear function may be derived to relate data from a given facility, device, or time period to other data.

In some instances, a determination that particular data corresponding to a given facility, device, or time period is different than data corresponding to one or more other facilities, devices, or time periods may indicate that data from the given facility, device, or time period is not to be used. In such instances, an instruction communication may be sent to a facility to reprocess a material, such as a sample.

In addition to receiving data from a data generator 140, the assessment system 105 may further collect one or more other data that may be used to assess, for example, a likelihood for transitioning into a particular state. For example, one type of other data may include inputs provided at a client device 130, such as inputs that indicate past-state data and/or current-state data, familial-state data and statuses, age, occupation, activity patterns, association with environments having particular characteristics, and so on. The other data may be received by way of one or more other data transmissions from an external system. In some embodiments, this data transmission may be encrypted prior to transmission and/or decrypted upon receipt. Optionally, this data may be transmitted over one or more network links, such as including transmission, at least in part, over a public communications network, such as the Internet.

Another type of other data may include data automatically detected at a client device 130. For example, a wearable client device may track activity patterns so as to estimate calories burned per day, or the wearable client device may estimate a pulse distribution, client temperature, sleep patterns and/or indoor/outdoor time. This data obtained directly by client device 130 may be directly transmitted (e.g., after a request and/or authorization handshake) to assessment system 105 and/or via another client device (e.g., via accessing health-data on a phone or computer device). Optionally, other data obtained directly by client device 130 may be transmitted over one or more network links, such as including transmission, at least in part, over a public communications network, such as the Internet. Optionally, other data obtained directly by client device 130 may be transmitted over at least a portion of a communication system. Optionally, other data obtained directly by client device 130 may be part of another data transmission.

Yet another type of other data may include record data, which may be stored, for example, at a record data store 165 at and/or associated with an external facility, such as one having provided an electronic request to perform an analysis or assessment pertaining to a client and/or one as identified via input at a client device 130. To illustrate, the other data may identify one or more client reported experiences and/or evaluation results for a client or may include a result of one or more tests.

In some instances, other data may include data pertaining to a different client. For example, it may be determined or estimated that a given client is related to another client. Such determination or estimation may be based on inputs detected at a client device identifying one or more family members (e.g., by name), and a data store may be queried to determine whether any clients match any of the family member identifications. Such relationship determination or estimation may alternatively or additionally be based on a data set analysis, such that a raw or processed data set from the given client is compared to a raw or processed data set from some or all other clients to identify, for example, whether any other clients share a threshold portion of a data set with the client. Upon detecting an above-threshold match, a percentage of value matching may be used to estimate a type of relationship between the clients. Upon identifying a related client, other data corresponding to the related client may be identified. For example, the other data may include a past or current state of the related client. The other data may be identified (for example) based on an input provided by the client or the related client or record data associated with the related client.

Thus, the assessment system 105 may have access to, for a given client, one or more data sets, data set availability modification data, client-reported data, record data, test data, activity data, and/or other types of data. These various types data may be detected, assessed, or otherwise evaluated, such as in one or more assessment processes. The detection and/or assessment may be performed, for example, partly or fully at assessment system 105. In some instances, the detection and/or assessment is performed in a partly or fully automated manner. In some instances, the detection and/or assessment involves processing of inputs provided by a reviewer or evaluator.

Through the interaction of multiple devices and entities, an assessment system 105 may receive data sets corresponding to individual clients. As illustrated, assessment system 105 may connect to each of one or more other systems or devices, using any method of communication or data exchange known in the art. For example, the assessment system 105 may communicate to other component within the assessment network 100 using a wired or wireless data connection that makes use of or is compliant with one or more Institute of Electrical and Electronics Engineers (IEEE) networking standards, such as 802.3 (Ethernet), 802.11 (Wi-Fi), or 802.16 (WiMAX), or other data communications standards such as IEEE 1394 (FireWire), Bluetooth, Universal Serial Bus (USB), Serial ATA (SATA), Parallel ATA (PATA), Thunderbolt, Fibre Channel, Small Computer System Interface (SCSI), GSM, LTE, etc. The data connections used may include one or more TCP/IP compliant interconnections, such as may be present on a private or public communications network, such as the Internet. The data connections may represent or include one or more intermediate systems or data connections between various other components of assessment network 100.

Upon detecting such a deviation or combination (or a threshold quantity thereof), the particular deviation and/or combination may be identified in a review-request communication and transmitted to an evaluation device 170. Evaluation device 170 may then present the identification to an evaluator 175 and detect input that is indicative of an estimated likelihood to associate with the deviation and/or combination, for example, as part of an optional review analysis process. A review-request response may be transmitted from evaluation device 170 to assessment system 105, for example, to provide the results of any review or input generated by an evaluator 175. The data included in review-request response may be used in report generation and may be included and/or otherwise influence the content of the final report transmitted in a report transmission.

A result generated by assessment system 105 may include a quantitative or qualitative (e.g., categorical) likelihood variable, such as one corresponding to a transitioning to a particular state. For example, the likelihood variable may include a percentage probability or range of transitioning into a particular state. As another example, the likelihood variable may be partitioned into three categories.

Assessment system 105 may generate an electronic report, that includes the result and/or that is selected based on the result. A report communication or transmission may include the report and be transmitted to client 125 or facility 120, such as by way of client device 130 or requestor device 110a. As an example, a report may identify one or more sparse indicators detected in a client data set and/or a bucket of each of one or more sparse indicator. A report may identify a likelihood (e.g., numeric or categorical) of transitioning to a particular state and/or a technique for having generated such a result. A report may identify types of data (e.g., particular data-set units and/or other type of data) used in the analysis. A report may identify a confidence in a result (e.g., a likelihood variable). A report may identify a recommendation (e.g., to contact a requestor or to receive a particular test or evaluation).

In some instances, a report must be approved (e.g., by a requestor 115a or 115b) before it is transmitted to a client device 130. A report-reviewing interface may, but need not, include a configuration to allow a reviewing entity to change or add to the report. A report-reviewing interface may further allow or require a reviewing entity to identify a time at which to send the report to a client.

Assessment system 105 may update and may have access to a variety of data stores, part or all of which may be remote from, co-localized with assessment system 105, and/or included in assessment system 105. One or more of the data stores may include a relational data store, such that data from one data store or structure within a data store may be used to retrieve corresponding data from another data store or structure.

Each of one, more, or all of the data stores may be associated with one or more access constraints. Access constraints applicable to a given data store may be stored as part of the data store or separately (e.g., in an access control data store). Access constraints that apply to one type of data may differ from access constraints that apply to another type of data. For example, account and client data may be associated with stricter access constraints than results data, to make it more difficult for a user, developer, or hacker to be able to link data to a particular individual. An access constraint may identify one or more individuals, devices, systems, and/or occupations permitted to access some or all data in a data store. An access constraint may include a rule, such as one that indicates that a user is permitted to access data pertaining to any of a group of users that the entity was involved in with respect to a transfer of a kit, or that indicates that any low-level authorized user is permitted to access de-identified data but not identifiable data, or that indicates that a high-level authorized user is permitted to access all data. As another example, access constraints may indicate that process data is to be hidden from external developers and available to internal users; that data-set unit, sparse indicator, and data set availability data is to be made available to all authorized external developers and internal users; and that client data is to be availed to authorized internal users and only availed to external developers to the extent to which each corresponding users represented in the data is a user of the developer (e.g., and that the client authorized such data access).

When different access rights apply to different types of data, a query protocol may be established to address instances where a query relates to each type of data. For example, a query may request Variable X for each client corresponding to Data Y, and Variable X and Data Y may correspond to different access constraints. As another example, a query may request a count of clients for which both Data Y and Data Z was detected, and Data Y and Z may correspond to different access constraints. One example of a query protocol is to use a most restrictive overlap of data constraints applying to the query. Another example of a query protocol is to permit use of an at least partly more relaxed access constraint so long as it relates to defining a client set or state and not to results to be returned or processed.

In some instances, an access constraint is configured to inhibit an identification of particular data (e.g., client identity). Such a constraint may relate to a precision of requested data. To illustrate, a constraint may be configured to permit a user to request and receive data identifying client locations, so long as the request is configured to not request too specific of a location and/or so long as the request corresponds to a number of client data elements sufficiently large to obscure (e.g., in a statistical result) a precise location. Compound queries may be more sensitive to potential identification concerns, such that one or more access constraints are configured to permit access to less precise data when multiple data elements are being requested.

Various data stores may be included in assessment network 100. The data stores may include, for example, an account data store 176, which may include login credentials for one or more users or clients and/or types of data access to be granted to each user or client; a process data store 177, which may identify facility analysis characteristics pertaining to particular data elements (e.g., identifying a facility, piece of equipment, and/or processing time); data sets store 178, which may identify one or more data sets associated with a given client or material, such as a sample; and one or more data-set expressions or signatures associated with a given client or material, such as a sample. The data stores may further or alternatively include a results data store 181, which may identify one or more sparse indicators identified by and/or one or more results generated by assessment system 105 that are associated with a given client or material, such as a sample.

The data stores may further or alternatively include a reports data store 182, which may include one or more report templates (e.g., each associated with one or more result types) and/or one or more reports to be transmitted or having been transmitted to a client device; and/or a relevance support data store 183, which may identify which types of data (e.g., data-set units, full or partial reference data sets, activity patterns, inputs, records, tests, etc.) are established to be, potentially, established not to be, or unknown whether to be relevant for evaluating a particular type of likelihood (e.g., a likelihood of transitioning into a particular state).

Relevance support data store 183 may include identifications of one or more content objects. The identifications may include, for example, web addresses, journal citations, or article identifiers. In some instances, an identification identifies one or more sources associated with the content object (e.g., scientist, author, journal, or data store). Content objects may be tagged with one or more tags, which may identify, for example, a sparse indicator, a data-set unit, a data set, and/or a type of assessment. In some instances, each of one or more content objects are associated with a score which may reflect a credibility of the content object. The score may be based, for example, on a publication frequency of a source, an impact factor of a source, a date of publication of the content object, and/or a number of citations to the content object.

Assessment network 100 may also include a user device 180 configured to detect input from a user 185. User 185 may be associated with an account or other authentication data indicating that access to some or all of the data is to be granted. Accordingly, user 185 may be able to interact with various interfaces (presented at user device 180) to view data pertaining to one or more particular clients (e.g., in an identified or de-identified manner), to view summary data that relates to data from multiple clients, to explore relationships between data types, and so on. In some instances, an interface may be configured to accept inputs from a user 185 so as to enable the user to request data pertaining to (for example) materials with sparse indicators in particular data-set units, particular sparse indicators and/or state likelihoods.

In some embodiments, the assessment system 105 may be involved in the generation of a report. The assessment system 105 may then send the report to client 125 or external facility 120, such as by way of client device 130 or requestor device 110a. In some embodiments, the assessment system 105 may be involved in the generation of a communication or report that may identify an anomaly subset of iteration data that has been determined by the assessment system 105. The assessment system 105 may then send this communication out to various components within the assessment network 100, such as facility 120, data generator 140, and external assessment device 190 used by the developer 195, in order to make the data processing workflow more accurate and efficient.

The assessment network 100 can also include an external assessment device 190 configured to detect input from a developer 195. Via such inputs, external assessment device 190 may send electronic requests for genetic and/or other data (e.g., relating to particular genes, a particular client and/or particular client inputs) to assessment system 105. Assessment system 105 may evaluate the request to determine, for example, whether a corresponding client 125 authorized such access (which may be verified via a communication exchange between assessment system 105 and client device 130) and/or whether such access is relevant to a purported type of analysis. If the evaluation indicates that access is to be granted, assessment system 105 may (for example) send an instruction communication to data generator 140 to conduct a new analysis of an existing sample, send a data request to a device (e.g., access control device 160b, client device 130) and/or retrieve data from a data store (e.g., and extract pertinent information from any larger data structure, such as extracting gene-specific data from a genome). Provision of such data may be conditioned upon or may require payment (e.g., by a client or developer) of a fee.

Workflows

This disclosure makes frequent reference to workflows. As previously discussed, the processing of data may involve multiple steps, and each step may include a process or task. These tasks may be performed by any entity or device. As referenced herein, a workflow may be broadly associated with a collection of processes or tasks. Additionally, a workflow may include a structure and definition for each of the processes or tasks within the workflow. In general, a workflow may be performed repeatedly, with each iteration of a workflow involving the performance of the tasks defined by the workflow. In some embodiments, each iteration of the workflow may correspond to a given client. For example, in some embodiments, each iteration may correspond to generating a likelihood variable for a given client and may involve various other entities (e.g., reviewers, facilities, etc.), which may be selected based on, for example, user preference, a physical location of a client device, and/or availability.

For the purposes of facilitating understanding, the following non-limiting example of a workflow is described within the context of FIG. 1. Specifically, generating outputs for users and/or requestors may involve multiple steps, each of which may include a process, which may be referred to herein as a task, of an entity and/or device. A workflow may include a structure and definition for these processes. For example, various workflows may include some or all of the following tasks:

Inputs are collected at client device 130, transmitted by client device 130, and received by assessment system 105, where the inputs correspond to a preliminary request to conduct an assessment based on a material and ensure that all required inputs have been received;

A same or different client device 130 (e.g., a wearable device) collects and transmits other data indicative of the client's activity or status;

Inputs collected at requestor device 110a, 110b and transmitted to assessment system 105 that correspond to a request for assessment for the client;

Access control device 160b at facility 120 collects and transmits record data of the client;

Distribution device 135 receives alert corresponding to new request and address information and confirms shipping of kit for sample collection to the client;

Client 125 receives kit, collects material and sends to data generator 140;

Assessment device(s) 145 collects data-set data, and access control device 160a sends facility data to assessment system 105;

Assessment system 105 detects any sparse indicators in data set(s) and/or any modifications in data set expression;

Assessment system 105 assigns any sparse indicators and/or data set availability modifications;

Evaluation device 170 collects inputs identifying an assignment of any sparse indicators and/or data set availability modifications as of an unknown likelihood;

Confirmatory facility testing of any sample associated with a sparse indicator and/or data set availability modification having a particular assignment at same or different facilities;

Assessment system 105 aggregates sparse indicator data, assignment data, record data, user or client inputs, other data, and/or activity or status data and generates one or more likelihood variables;

Assessment system 105 generates electronic report with the one or more likelihood variables;

Evaluation device 170 and/or requestor device 110a collect inputs indicating that the electronic report is approved for transmission to client device 130; and Assessment system 105 transmits the electronic report to client device 130.

In some embodiments, a workflow may include a task order that indicates that, for example, a first task is to be completed prior to performance of a second task, though a workflow may alternatively be configured such that at least some tasks may be performed in parallel. In some embodiments, one or more tasks in a work flow are conditional tasks that need not be performed during each iteration of the work flow. Rather, whether a conditional task is to be performed may depend on a circumstance, such as whether a result from a prior task is of a particular type or exceeds a threshold.

Processing of Sparse Indicators

In some embodiments, the workflow for analyzing genetic data may include processes or tasks directed at the detection and identification of sparse indicators. An overview of the detection and identification of sparse indicators is provided below. Additional detail on this topic can be found in U.S. Non-Provisional patent application Ser. No. 15/163,191, titled "UNIT-SPECIFIC DATA REPOSITORY QUERIES FOR RESTRICTED PROCESSING OF EXTERNAL ASSESSMENT SYSTEM REQUESTS", filed May 24, 2016, which was is hereby incorporated by reference in its entirety for all purposes.

For an iteration of the workflow, one or more sparse indicators can be determined by comparing generated data (e.g., a client data set including a client's sequenced genome) against reference data set (e.g., a reference genome).

More specifically, a set of reads may be received from a data source (e.g., laboratory). The set of reads may be obtained from using a technique and/or device process client's biological material to identify an ordered set of identifiers (e.g., bases). The set of reads may thus correspond to a particular client.

Each read of the set of reads can be aligned to a portion of a reference data set (e.g., reference genome), which may include one or more vectors, with each vector including a plurality of identifiers. The alignment may include, for example, preliminarily aligning the read to each of one or more portions of the reference data set, and generating a score for the preliminary alignment based on a comparison between identifiers in the portion of the reference data set and identifiers in the read (e.g., with higher scores being generated in response to stronger matches). An alignment can then be identified based on the scores (e.g., to select an alignment associated with a top score).

Thus, each position of the reference data set may be associated with an identifier from one or more reads. These identifiers can be collectively assessed to identify an identifier for a corresponding position in a client data set. For example, an identifier of a client data set may be defined to be an identifier most represented across the reads and/or with a collective representation of the identifier and a complementary identifier exceeding a threshold. The generated client data set can thus include one or more vectors, with each vector including a plurality of identifiers. For example, each of the reference data set and client data set can identify identifiers (e.g., bases) in each of one or more data-set units (e.g., genes)

Individual identifiers of the client data set can be compared to corresponding identifiers (associated with a same and/or corresponding position) in the reference data. Each difference between the client data set and the reference data set can be defined to be sparse indicator associated with the client data set.

Different types of sparse indicators (e.g., variants) may be identified this way, such as a one-element sparse indicator representing a single data element different from a reference data set (e.g., a single nucleotide polymorphism), or a structural sparse indicator (e.g., a structural variant, such as a copy-number variation, inversion, duplication or deletion) representing a set of consecutive data elements different from a reference data set (e.g., a structural variant). A structural sparse indicator may be detected upon determining (for example) that a series of elements in a data set generally differ from those in a reference data set or that values in a coverage set change across the set so as to indicate that a portion of the reference data set is over- or underrepresented in the data set.

After the sparse indicators are identified, the workflow may further involve the system classifying each sparse indicator or assigning it to a data bucket. Each sparse indicator may be assigned to a bucket which may reflect a predicted impact of the detected difference. In some instances, a set of buckets are defined. Each of one, more or all of the buckets may correspond to a predicted likelihood that a client will progress to a given state. A state may include, for example, utilizing a full memory bank, a condition (e.g., cancer), reduced bandwidth, and/or a connection drop. Thus, buckets may reflect whether and/or a degree to which a difference causes the state (e.g., reflecting memory requirements, whether the difference is (e.g., and/or is likely to be) pathogenic or benign), consumes bandwidth, and/or impairs a connection's stability). For each client, a determination as to how many sparse indicators were assigned to one or more particular buckets may be used to generate a result that identifies a state-progression prediction.

The assignment of individual sparse indicators to various data buckets may be performed in various ways. For example, the system may reference a look-up table may include a set of entries, each of which corresponds to a sparse indicator. The system may reference the table using a position and identifier for each sparse indicator, or by a range of positions and type of sparse identifier (e.g., type of structural sparse identifier and/or one or more corresponding position ranges in a reference data set). The look-up table may then inform the system of the classification or bucket assignment listed for each sparse indicator. Furthermore, the table may also include a confidence associated with such an assignment. For instance, from observations over time it may be determined that a specific sparse indicator at a specific location should be associated with a certain assignment at a 99% confidence. Thus, in order to classify various sparse indicators, the system may need access to information regarding types, identities, values, assignments, and/or confidence metrics associated with various sparse indicators that can be identified from the generated data. This information may also be used to determine classifications or bucket assignments for various types of sparse indicators (e.g., structural sparse indicators), such as a sparse indicator that indicates that elements from Position X to Position Y are not present in a client data set. In some embodiments, the classification may involve determining whether each of the sparse indicators is a deviation that is pathogenic in nature (e.g., that particular difference between the client data set and the reference data set may lead to increased probabilities of certain diseases arising). In some embodiments, a machine-learning model can be trained in order to classify and assign sparse indicators to various data buckets. The machine-learning model may then be applied to individual sparse indicators in order to evaluate the types, identities, and values of those sparse indicators and assign them into a data bucket. The model may also be able to determine any confidence levels associated with the prediction or the existence of those sparse indicators.

In some embodiments, two or more corresponding portions of a reference data set are identified before processing of a read (so as to be defined as a "first pre-identified portion" and a "second pre-identified portion"). The two or more corresponding portions can include, for example, a pseudogene and a corresponding gene or part thereof. The corresponding portions may be related in terms of identifier identity. For example, the corresponding portions can be portions with data with identifiers that are similar (e.g., to at least a defined degree) to each other. For example, when comparing corresponding identifiers between the first and second pre-identified portions (the corresponding positions having a same portion-relative position relative to a beginning of the portion), the identifiers may match each other (e.g., be the same as and/or correspond to each other) for at least 80%, 90%, 95% or 99% of the portion-relative positions.

In some instances, the corresponding portions are the same length as each other. The corresponding portions may have a length that is (for example) at least (for example) 5, 10, 20, 50 or 100 times as long as a minimum or average length of a read that is aligned and used as part of a sparse-indicator detection process. The corresponding portions may have a length that is at least (for example) 1,000, 2,000, 5,000, 10,000 or 20,000 identifiers.

A set of reads can be received from a data source, which generated the set of reads using a processing of a first type performed on a sample. Alignments of each of the set of reads can be performed using all or part of the reference data set (e.g., that is larger than the two or more corresponding portions). While alignment rules may indicate that, generally, each read is to be aligned to a single part of the reference data set, in some instances, this constraint is relaxed when a top alignment (e.g., associated with a highest score across multiple potential alignments) overlaps (e.g., entirely, by at least a threshold length or percentage or at all) with one of the corresponding portions. The relaxed constraint may allow the read to also be aligned with the other of the corresponding portions.

For each portion of the two or more corresponding portions, the reads at least partly aligned to the portion can be assessed to identify—for each position in the portion—one or more client identifiers for the position that are represented by identifiers aligned to the position in the reads. The identification can be based on, for example, a distribution identifiers across the reads (e.g., to include an identifier in the one or more client identifiers if the identifier is represented at the position in at least a threshold percentage of the aligned reads).

For each client identifier of the one or more client identifiers, it can be determined whether the client identifier is the same as (and/or, in some instances, complementary to) an identifier at corresponding position in the reference data set. If so, the client identifier can be characterized as a sparse identifier (e.g., associated with a position of the client identifier and the identifier itself). Each identified sparse indicator may be categorized.

For each of the two or more corresponding portions, the category/categories for any sparse indicators can be evaluated via a verification condition. In the case where no sparse indicators exist and/or if the category/categories for any sparse indicators are such that the data-verification condition is not satisfied (e.g., each category avoiding one or more pre-identified categories, a count of sparse indicators in each or a total of one or more pre-identified categories being under a predefined threshold, etc.), then a state-transition likelihood can be generated based on neither, either or both of the results (in terms of sparse indicator identification and classification). When it is determined that the data-verification condition is satisfied, a communication may be generated and transmitted (e.g., to a data generator or data source) that corresponds to a request to verify the read. The communication may identify a client associated with the reads and request that a second type of processing be performed on the sample. For example, the second type of processing may include a processing type that produces sequence reads of longer length, thereby providing an indication as to with which of the two or more corresponding portions the read is to be aligned.

Figure 2:
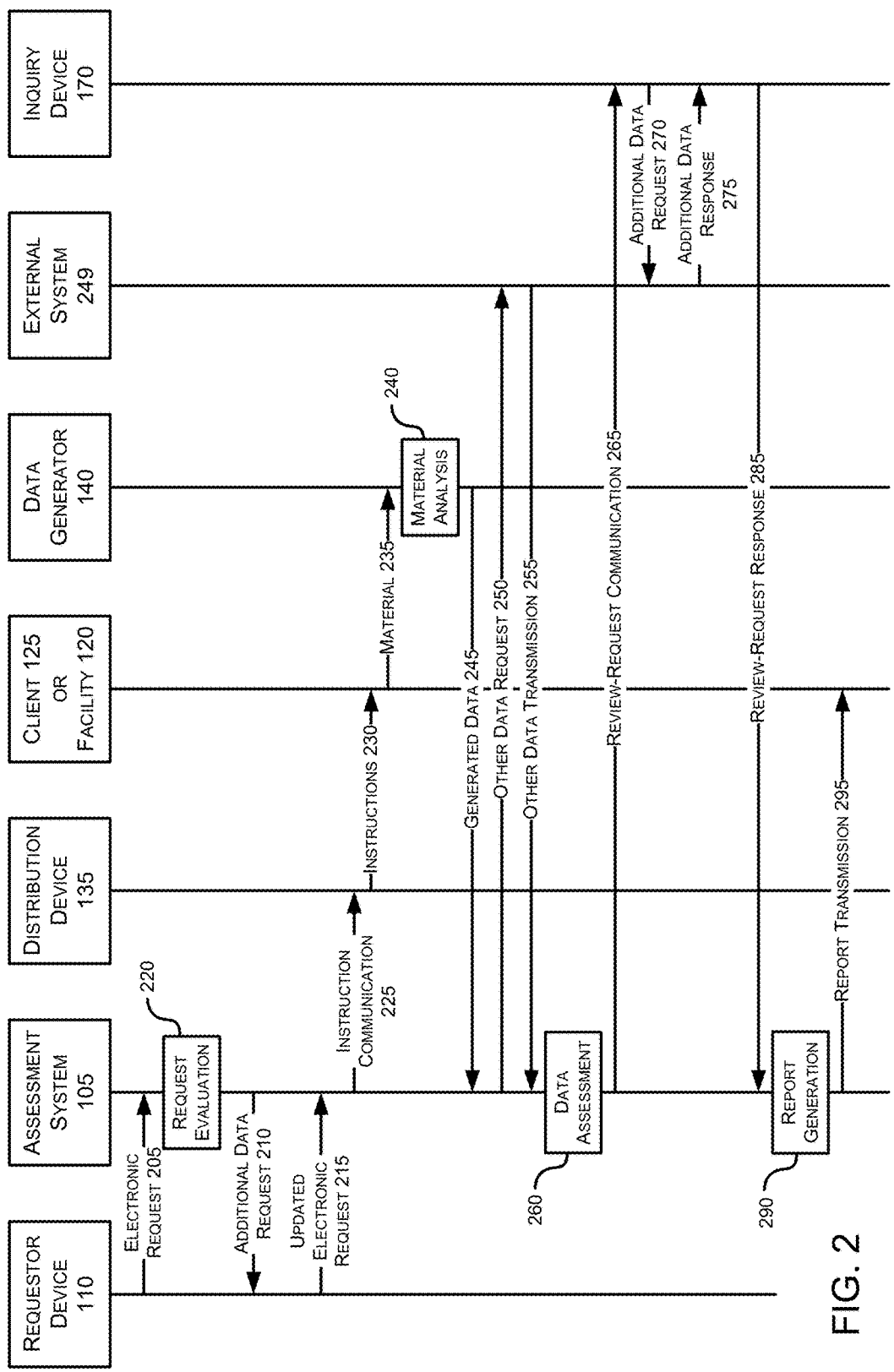
FIG. 2 shows a communication exchange between systems and devices of an data processing network, in accordance with some embodiments.

FIG. 2 illustrates interactions between various systems or components of an assessment network to illustrate the flows of data and materials, for example. Assessment system 105 may, for example, receive an electronic request 205 from a requestor device 110. In some embodiments, the request 205 may include instructions to conduct a data-set analysis. Optionally, request 205 may be encrypted prior to transmission; such an electronic request may be decrypted upon receipt. Request 205 may identify, or otherwise indicate, one or more states to be evaluated during the analysis and/or during an assessment. Request 205 may identify a client and/or include additional data pertaining to the client, such as client-identifying data.

Once request 205 has been received from a requestor device 110, the assessment system 105 may evaluate, such as at block 220, the request 205 to ensure that all required data has been provided and that all required data pertaining to the client has been identified (e.g., via the request, a preliminary request and/or stored data). If the assessment system 105 determines that all required information has not been identified, an additional data request 210 for such information may be transmitted to the requestor device 110. The request 205 may be updated with this information and an updated electronic request 215 may be transmitted back to assessment system 105. In various instances, an object provided to a user depends on an analysis requested, whether, and what kind of, new data-generation processing of a material is required for the analysis, a number of data-set units being assessed (e.g., and whether they have been previously assessed), a number and/or type of analyses being requested, a number and/or type of analyses previously requested, a number and/or type of analyses predicted to be requested subsequently, a state for which a progression prediction is being requested, whether a user is granting other entities' access to the client's data or results, whether a user is authorizing additional analyses to be performed on the client's data, and/or whether a user is granting permission to send offers to request user access to results or reports other than those initially being requested.

When all required information has been provided, assessment system 105 may send an instruction communication 225 to a distribution device 135. Optionally, the instruction communication 225 may be encrypted prior to transmission; such an encrypted communication may be decrypted upon receipt. Optionally, the communication 225 may be transmitted using communications system 108 and/or over one or more network links, such as including transmission, at least in part, over a public communications network, such as the Internet. The communication 225 may include, for example, a name and address of client 125 and, in some instances, an indication as to what is to be provided to client 125 or facility 120 for collection of a material for subsequent analysis. For example, a request 205 may indicate a type of analysis that is to be performed on a material (e.g., an analysis pertaining to a likelihood of getting one or more particular types of states) and/or a type of material (e.g., type of sample) that is to be analyzed. The communication 225 may identify the type of analysis, type of material, and/or kit associated with collection of the material. The communication 225 may thus facilitate and/or trigger a physical distribution of instructions 230, which may include a kit or other sample collection materials, to the client 125. The instructions 230 may include, for example, instructions as to how to collect a material, a container for storing the material and/or information pertaining to an instruction or type of analysis to be conducted. Alternatively, the instructions 230 may be provided to a facility 120, which may aid client 125 in obtaining the material.

The material 235 from the client 125 may then be directed to and received at a data generator 140 for material analysis 240. The data generator 140 may be, for example, part of a facility. The data generator 140 may include one or more assessment devices configured to generate data reads, data elements, or data sets for various data-set units using the material 235 as part of analysis 240. For example, an assessment device may include a data-characterizer device (e.g., sequencer and/or polymerase chain reaction machine). The data generator 140 may further include one or more devices, such as a desktop or laptop computer. Generated data 245 generated by or at one or more devices may be stored at a data store, which may be remote from all data generator devices or part of a data generator device. The generated data 245 may, for example, include identifying client information (e.g., a name and address), facility information (e.g., location and name), device specifications (e.g., manufacturer and model of assessment device) and data.

In some instances, data is optionally collected or requested from one or more external systems 249. Thus, assessment system 105 may transmit one or more other data requests 250 and one or more other data transmissions 255 may provide the other data. For example, one or more data sets and/or one or more processed versions thereof (e.g., identifying one or more sparse indicators) corresponding to an existing or new client may be received from an external system 249. As another example, assessment system 105 may transmit a client data set to an external system 249, and external system 249 may then return a result of an assessment of the client data set. As yet another example, other data may include a data set (or results based on such data) corresponding to another individual (e.g., an entity related to a client and/or an entity sharing a characteristic with a client). The other individual may be, for example, identified based on input from the client and/or automatically identified (e.g., based on a query of a data store to identify clients associated with inputs or results indicating a shared characteristic or relationship). In some instances, a state assessment variable may be generated based on data from multiple other people, and the data for each other person may be weighted based on (for example) how closely related the person is with a client and/or how many or which characteristics the person shares with a client.

The generated data 245 may include a plurality of data reads, data elements, or sets (e.g., each data read in the plurality of data reads corresponding to a same client, or at least some of the plurality of data reads corresponding to different clients). In various instances, data 245 may be transmitted to assessment system 105 in a batch-mode, in a streaming mode, in real-time as data is produced, and/or upon request. The data 245 may also be stored at a data store local or remote to data generator 140. A given transmission or stream may include data that corresponds to a single, or in other instances to multiple, client, sample, and/or data reads. In one instance, as data reads are generated by the data generator 140, a data set is generated so as to include each new data read and one or more identifiers (e.g., of a client, sample, time and/or facility device). The data may then be transmitted via a discrete communication (e.g., via FTP, over a webpage upload, email message, or SMS message) to assessment system 105. In one instance, the data may then be appended to a stream that is being fed to assessment system 105.

In addition to receiving data 245, the assessment system 105 may further collect one or more other data that may be used to assess, for example, a likelihood for transitioning into a particular state. The other data may be received by way of one or more other data transmissions 255 from external system 249. Optionally, other data transmission 255 may be encrypted prior to transmission; such an encrypted transmission may be decrypted upon receipt. Optionally, other data transmission 255 may be transmitted over one or more network links, such as including transmission, at least in part, over a public communications network, such as the Internet.

Another type of other data may include data automatically detected at a client device 130. For example, a wearable client device may track activity patterns so as to estimate calories burned per day, or the wearable client device may estimate a pulse distribution, client temperature, sleep patterns and/or indoor/outdoor time. This data obtained directly by client device 130 may be directly transmitted (e.g., after request 250 and/or authorization handshake) to assessment system 105 and/or via another client device (e.g., via accessing health-data on a phone or computer device). Optionally, other data obtained directly by client device 130 may be transmitted over one or more network links, such as including transmission, at least in part, over a public communications network, such as the Internet. Optionally, other data obtained directly by client device 130 may be transmitted over at least a portion of a communication system. Optionally, other data obtained directly by client device 130 may be part of other data transmission 255. Accordingly, the assessment system 105 may have access to, for a given client, one or more data sets, data set availability modification data, client-reported data, record data, test data, activity data, and/or other types of data.

Some or all of this data may be detected, assessed, or otherwise evaluated, at block 260, such as in one or more assessment processes. Data sets may be evaluated to detect and assess sparse indicators, for example. The detection and/or assessment at block 260 may be performed, for example, partly or fully at assessment system 105. In some embodiments, the assessment at block 260 may be performed in a distributed manner among a plurality of machines associated with the assessment system 105. In some instances, the detection and/or assessment at block 260 is performed in a partly or fully automated manner. In some instances, the detection and/or assessment at block 260 involves processing of inputs provided by a reviewer or evaluator.

In some embodiments, the detected sparse indicators can be assessed in order to determine a state transition likelihood associated with particular sparse indicators. Any particular sparse indicators and/or combination of sparse indicators may be identified in a review-request communication 265 and transmitted to an evaluation device 170. The evaluation device 170 may then present the identification to an evaluator and detect input that is indicative of an estimated likelihood to associate with the sparse indicators, for example, as part of an optional review analysis process. To perform this review analysis process, the evaluation device 170 may send an additional data request 270 to the external system 249 for any information that may be needed to perform the analysis. The external system 249 may transmit an additional data response 275 back to the inquiry device 170 with that information.

A review-request response 285 may be transmitted from evaluation device 170 to assessment system 105, for example, to provide the results of any review or input generated by the evaluator. The data included in review-request response 285 may be used in report generation process of block 290 and may be included and/or otherwise influence the content of the final report transmitted in report transmission 295. Generation of a report, at block 290, may be performed using the results of data assessment of block 260. A report transmission 295 may include the report and be transmitted to client 125 or facility 120.

Figure 3:
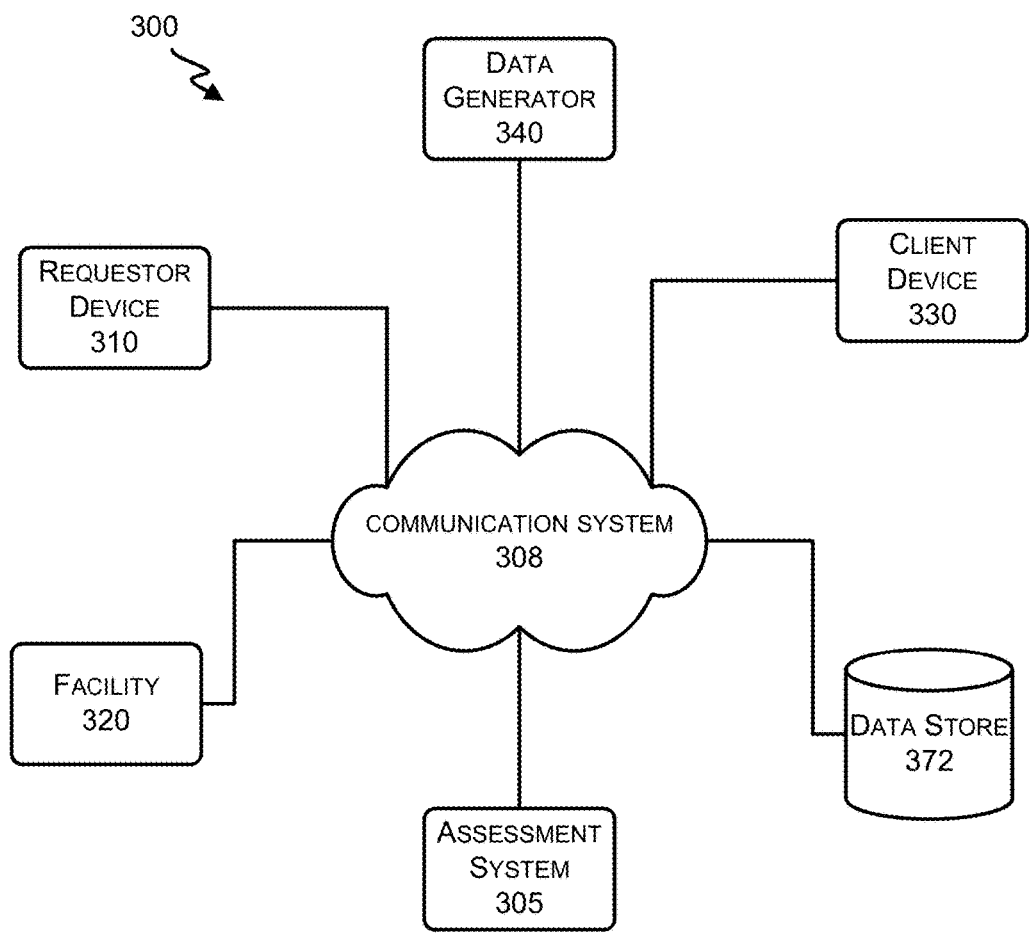
FIG. 3 shows a representation of an example communication network, in accordance with some embodiments.

FIG. 3 illustrates an example communication network, such as the assessment network 300. The assessment network 300 may, but need not, correspond to assessment network 100 shown in FIG. 1. Through the interaction of multiple devices and entities, an assessment system 305 may receive data sets corresponding to individual clients. As illustrated, assessment system 305 may connect, via communication system 308, to each of one or more other systems or devices. Assessment network 300 may also include additional systems or devices, as illustrated in FIG. 3. For example, assessment network 300 may include requestor device 310, facility 320, client device 330, data generator 340, and data store 372, in addition to other systems or devices not explicitly depicted in FIG. 3.

Data may be exchanged between various systems or devices of assessment network, such as by way of communication system 308. Communication system 308 may, for example, include one or more data communication systems or networks, such as a wired or wireless data connection that makes use of or is compliant with one or more Institute of Electrical and Electronics Engineers (IEEE) networking standards, such as 802.3 (Ethernet), 802.11 (Wi-Fi), or 802.16 (WiMAX), or other data communications standards such as IEEE 1394 (FireWire), Bluetooth, Universal Serial Bus (USB), Serial ATA (SATA), Parallel ATA (PATA), Thunderbolt, Fibre Channel, Small Computer System Interface (SCSI), GSM, LTE, etc. Communication system 308 may include one or more TCP/IP compliant interconnections, such as may be present on a private or public communications network, such as the Internet. Communication system 308 may further include servers, systems, and storage devices in the cloud. Communication system 308 may represent or include one or more intermediate systems or data connections between various other components of assessment network 300. Additionally, communication system 308 may represent a direct connection between various other components of assessment network 300, such as a direct connection between assessment system 305 and data store 372, which may optionally allow for communication with data store 372 by other components of assessment network 300 only by way of assessment system 305, for example. It will be appreciated that data store 372 may include one or more data stores, which may optionally be linked or otherwise configured or organized to allow for efficient retrieval and storage of data by reference to different entries in particular data stores or data tables. For example, data store 372 may comprise a relational database or data store, in some embodiments.

One or more of the devices or systems of assessment network 300 may be present at a single location or each may be present at various different locations and be in data communication with one another via communication system 308, depending on the specific configuration. For example, facility 320 and data generator 340 may be at a same location. Requestor device 310 may further be present at facility 320, such as if possessed by a requestor personnel, for example. Similarly, client device 330 may also be present at data generator 340 or facility 320, such as if possessed by a client, for example. In some embodiments, one or more devices or systems of assessment network 300 may be mobile devices, such as a smartphone, tablet computer, laptop, or other compact device, which may facilitate transport between locations or with a user or client. Use of mobile devices may, for example, be advantageous for allowing input to be entered in real-time and/or on request from any location in order to facilitate expedient processing and/or analysis of data or generation of state assessments.

In one instance, assessment system 305 receives a request communication (e.g., via communication system) from a requestor device 310 that identifies a client. Client identifying authentication and/or other information can be received from a client device (e.g., which, in some instances, is also requestor device 310). Assessment system 305 may then prime data generator 340 to detect a material associated with the client and generate a set of reads based thereupon.

As previously described, the assessment system 305 may process the reads associated with each client and generate one or more client data sets. With each client data set, the assessment system 305 can detect one or more sparse indicators (e.g., differences) between the client data set and the reference dataset. A sparse indicator may be defined for each difference so as to identify a type of difference observed (e.g., what identifier was present in the client data set as opposed to a reference data set) and a position (e.g., with respect to the reference data set and/or along one or more data-set units) at which the difference was observed.

Each sparse indicator may be assigned to a bucket which may reflect a predicted impact of the detected difference. Each of one, more or all of the buckets may correspond to a predicted likelihood that a client will progress to a given state, which may include, for example, utilizing a full memory bank, a condition (e.g., cancer), reduced bandwidth, and/or a connection drop. A determination as to how many sparse indicators were assigned to one or more particular buckets may be used to generate a result that identifies a state-progression prediction. The result may be transmitted to requestor device 310 and/or client device 330.

Figure 4:
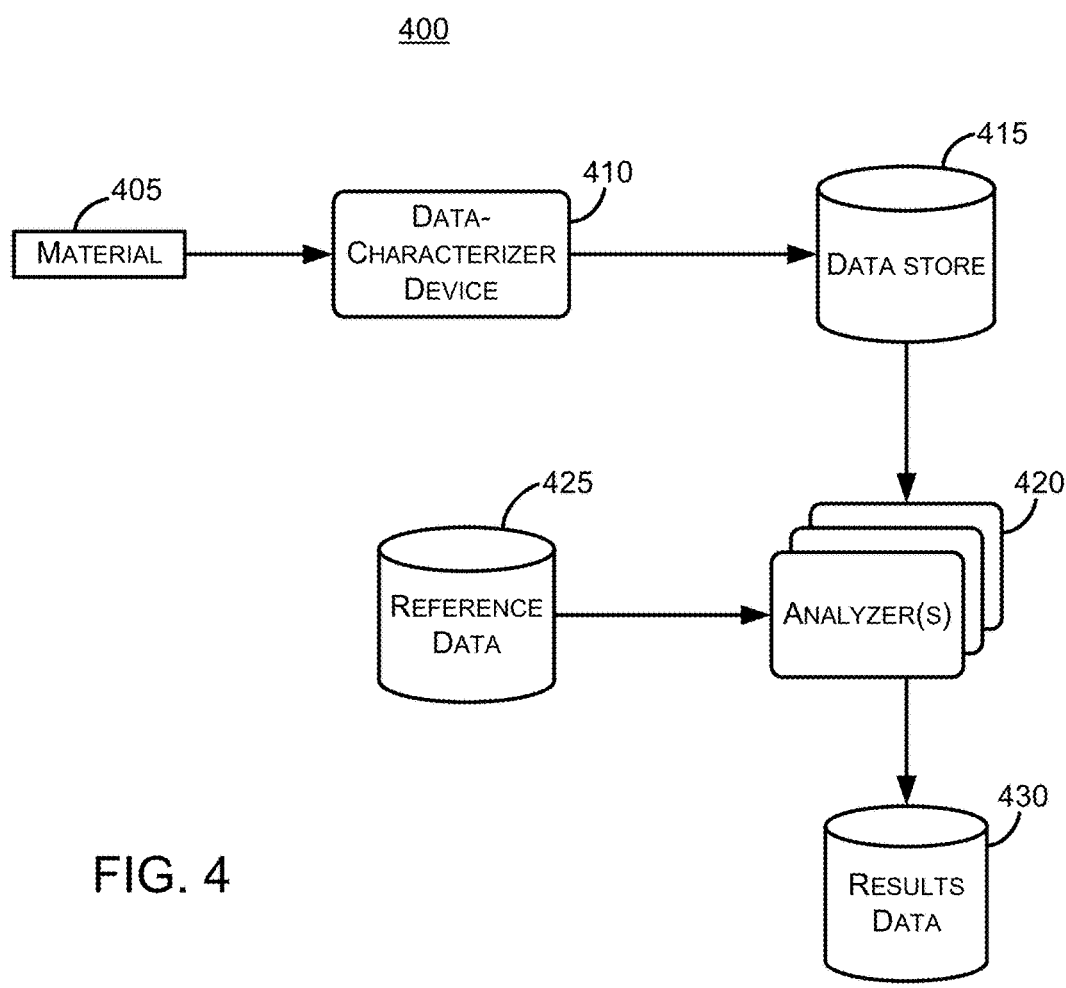
FIG. 4 shows a data flow, in accordance with some embodiments.

FIG. 4 illustrates a data flow embodiment 400. Initially, a test material 405 is obtained from a client. As described above, the material 405 may be obtained directly by the client using a collection kit. A client may be able to obtain the material themselves, particularly if the material is easy to collect. Alternatively or additionally, material 405 is obtained at a facility. Obtaining material 405 at a facility may be useful if the material is more difficult to obtain, or if chain-of-custody is a concern.

Material 405 is assessed by a data-characterizer device 410, which may generate a plurality of data sets, including coverage data sets and identifier data sets. As the data sets are determined, they may be stored in data store 415 for subsequent analysis.

Data-characterizer device 410 and data store 415 may be located at a same location, such as a facility. Alternatively, data-characterizer device 410 and data store 415 may be remote from one another. In such a configuration, transmission of data sets from data-characterizer device 410 to data store 415 may occur using any of a variety of data communication standards and/or protocols. In one example, data sets are transmitted from data-characterizer device 410 over a wired and/or wireless network to reach data store 415. In another example, data sets are stored by data-characterizer device 410 directly to a storage medium, such as a flash drive or hard drive, which may be used to facilitate relaying data sets to remote data store 415. Optionally, data store 415 may comprise the storage medium. Data sets stored in data store 415 may be analyzed by data set analyzer 420. Data set analyzer 420 may be located at a same or different location from data-characterizer device 410 and/or data store 415.

Depending on the particular configuration, data sets generated by data-characterizer device 410 and/or stored in data store 415 may be analyzed individually, in real-time as the data sets are produced, or in batches, such as upon completion of a plurality of data sets. Data set analyzer 420 may utilize reference data stored in reference data store 425 in analysis of the data sets generated by data-characterizer device 410 and/or stored in data store 415.

A variety of analyses may be performed on the data sets by data set analyzers 420. For example, data set analyzer 420 may align each read in a data set to a portion of one or more reference sets. Data set analyzer 420 may also generate coverage data and/of identifier data using reads from the data set. Upon completion of the analysis, the information corresponding to the data sets (e.g., coverage data and/or identifier data) and/or alignment indications may be transmitted to and/or stored in one or more results data stores 430, which may correspond to a portion of data store 372.

It will be appreciated that data set analysis may be resource intensive, and thus a plurality of data set analyzers 420 may be used during the analysis process to distribute the resource burden, for example, and/or increase the rate at which data sets may be analyzed. For example, if a plurality of alignments are to be evaluated, such as by determining a potential alignment of an individual data set against multiple reference data sets, it may be desirable to distribute the tasks among multiple data set analyzers 420. Load balancing between a plurality of data set analyzers 420 may be performed to further enhance the use of resources, for example. Additionally, it may be desirable to compare the data sets stored in data store 415 against multiple reference data sets, such as from related family members or from people sharing one or more characteristics, as described above, and comparisons of the data sets with different reference data sets may be performed by different data set analyzers.

Additionally or alternatively, data sets may be analyzed by one or more data set analyzers 420 to identify one or more sparse indicators. Additionally or alternatively, data sets may be analyzed by one or more data set analyzers 420 to categorize each data set, alignment, or detected sparse indicator. Additionally or alternatively, data sets may be analyzed by one or more data set analyzers 420 to score each data set, alignment, or detected sparse indicator. Again, sparse indicators, categories, and scores may be transmitted to and/or stored in results data store 430 (which may be included in data store 372).

Figure 5:
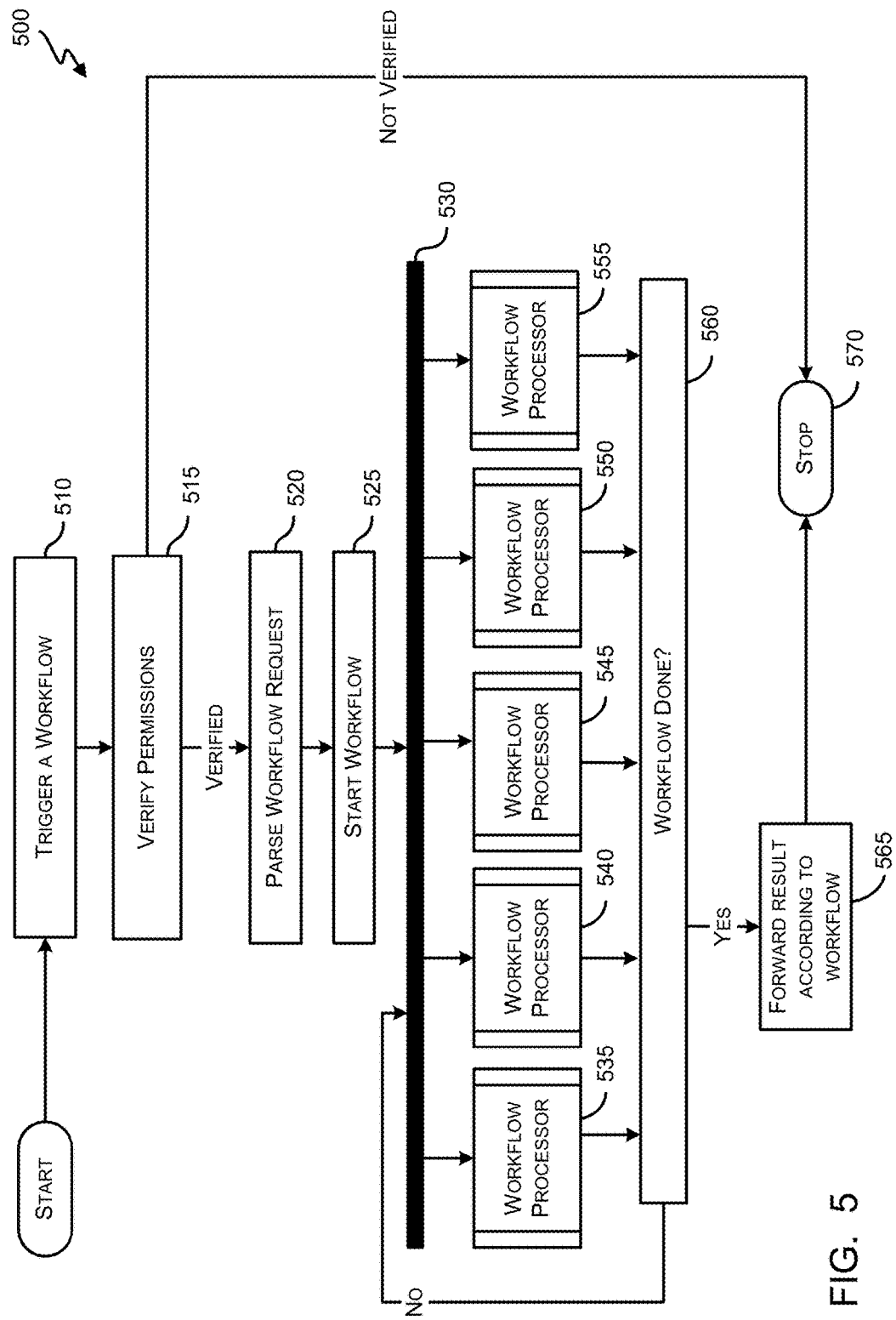
FIG. 5 shows an illustration of a work flow iteration, in accordance with some embodiments.

FIG. 5 shows a representation of an embodiment of a process 500 for processing tasks in the assessment network 100.

Additionally or alternatively, data sets may be analyzed by one or more data set analyzers 420 to identify one or more sparse indicators. Additionally or alternatively, data sets may be analyzed by one or more data set analyzers 420 to categorize each data set, alignment, or detected sparse indicator. Additionally or alternatively, data sets may be analyzed by one or more data set analyzers 420 to score each data set, alignment, or detected sparse indicator. Again, sparse indicators, categories, and scores may be transmitted to and/or stored in results data store 430 (which may be included in data store 372).

The process starts when an event triggers a first work flow as shown at block 510. Any number of events occurring internal to the assessment network 100 and external to the assessment network 100 may trigger a first work flow in any number of ways. Each of the assessment system 105, a requestor device 110, a client device 130, a distribution device 135, a facility data generator, an evaluation device 170, a user device 180, and an external assessment device 190 may trigger a work flow, for example. For instance, the assessment system 105 may trigger a work flow when it receives an electronic request 205. A requestor device 110 may trigger a work flow by transmitting electronic request 205. A user device may trigger a work flow based on inputs collected. A data generator 140 may trigger a work flow upon receipt of a sample. Other examples are possible and it will be appreciated from the present description that any one or more data transmissions between various devices and systems of assessment network 100 may trigger a work flow. It will also be appreciated that various work flows may be initiated sequentially or simultaneously, depending on the particular need for completion of one work flow to complete before another work flow may begin. In addition, additional work flows may be triggered while in the midst of processing one work flow. In some embodiments, an assessment system or assessment device manages and/or coordinates triggered work flows. Optionally, task start times may be tracked, as described above, and triggering a work flow may include tracking the start time of tasks associated with the work flow.

Some task work flows may require verification of permissions and/or authorizations, such as depicted at block 515, before the work flow is permitted to begin. For example, a transmission of record data of a client may require explicit authorization from a client or a requestor before the transmission may begin, for example, due to the sensitivity of information that may be included in the record data. As another example, transmission of information of a client to an external assessment device may also require client permission. In this way, permission verification may prevent unanticipated or unauthorized transmission of information to a particular work flow processor for which such transmission may be undesirable. Timing of permission request and verification may further be tracked, such as to allow identification of bottlenecks in work flow and/or task processing associated with permission verification. U.S. patent application Ser. No. 15/133,089, filed on Apr. 19, 2016 and U.S. Provisional Applications 62/150,218, filed on Apr. 20, 2016, and 62/274,660, filed on Jan. 4, 2016, disclose details regarding various work flow processes, and are each hereby incorporated by reference in its entirety for all purposes.

As illustrated in FIG. 5, if permissions are not verified, the work flow may be stopped, at block 570. If permissions are verified, the work flow may proceed to block 520. It will be appreciated that not all work flows require permission verification, and so block 515 may be considered to be optional.

Depending on the particular work flow initiated, the work flow request may require parsing, at block 520, to ensure that various portions of the work flow may be handled appropriately. Parsing may include determining that all required inputs, data, and/or materials needed for completing the work flow are available. In the event that additional inputs, data, and/or materials are needed, the work flow may be returned to the triggering device to request the additional inputs, data, and/or materials, for example. Parsing may also include aspects of load-balancing. Parsing may also include, for example, analyzing the work flow request and associated data and/or materials to ensure the data, materials and/or multiple individual sub-work flow processes are directed to an appropriate work flow processor 535, 540, 545, 550, 555, etc. Task start times may optionally be tracked based on completion of parsing a work flow request, for example.

In one embodiment, a work flow may correspond to performing a data set analysis on a sample, which may include dividing the sample into sub-samples. The sub-samples may, for example, be redundantly analyzed to ensure accuracy. Parsing 520 may include identifying necessary resources for completing a particular work flow.

After parsing the work flow request, the triggered work flow is started, at block 525. Optionally, synchronizer 530 oversees the processing of individual work flow processes by work flow processors. Optionally, tracked task start times may correspond to times at which the triggered work flow is actually passed to a work flow processor.

Some task work flows may include multiple individual work flow processes, such as a sequencing work flow for sequencing data-set unit data or sparse indicator data from a sample, where each individual work flow process may correspond to, for example, one or more data sets. These individual work flow processes may be performed in series, for example, such as if a particular work flow process requires input from a previous work flow process. The individual work flow processes may alternatively be performed in parallel, for example, if the separate work flow processes do not rely on an a result from another work flow process that may be performed simultaneously. Additionally, individual work flow processes may be started and completed without regard to other work flow processes that may be operating. Upon a work flow processor 535, 540, 545, 550, 555 completing the designated tasks, at 560, the work flow may be evaluated to determine whether the work flow is completed. If additional processing is required, the work flow may return to synchronizer 530 for appropriate queuing. If no additional processing is required, the work flow result may be forwarded as appropriate, at 565. Once a particular work flow is forwarded, the task associated with the work flow may stop, at block 570. Optionally, task stop or end times may be tracked based on the time at which a work flow proceeds to stop at block 570.

Assessment system 105 may store task start and completion times, and/or task completion time periods (i.e., a difference between corresponding task completion and task start times) in process data store 177 in association with an identifier of the corresponding task and an identifier of a corresponding work flow iteration (e.g., an identifier of a client or sample). Assessment system 105 may collect task start and completion times that correspond, for example, to a given time period, facility, user or client group, analysis type, etc. and analyze the data at a population level. Through such analysis, assessment system 105 may identify average, median, or mode completion time periods for individual tasks so as to identify tasks, facilities, or entities associated with work flow processing delay. Further or alternatively, assessment system 105 may identify a backlog for individual tasks by identifying a number of "open" tasks for which a start time has been identified but for which no completion time is identified. Tasks, facilities, and/or entities associated with high backlog may then be identified.

Such task completion time monitoring may be performed automatically and/or in response to a query communication from user device 180. For example, assessment system 105 may determine, for each handling entity (e.g., facility, distribution device, reviewer, or facility) a portion of tasks completed by a first threshold time identified for a given task. Upon detecting that the portion exceeds a second threshold, an alert communication may be transmitted to user device 180 and/or a device of an associated entity. As another example, assessment system 105 may present a statistic (e.g., mean) corresponding to a processing time of each task in a work flow. The presentation may be interactive, such that more details about a statistic may be presented in response to a user selection of the statistic. For example, the statistic may be broken down by entity and/or task start time period, or more detailed information (e.g., a distribution or list of start and completion times) may be presented.

In some instances, data transmitted from assessment system 105 to user device 180 may relate to data queries received from user device 180. The query may, in some instances, include one that specifically or implicitly identifies one or more data-set units. For example, identification of a given kit or assessment may be associated with one or more data-set units. Assessment system 105 may identify data that any access constraints indicate are accessible to the user, and present high-level population data. For example, assessment system 105 may identify a portion of clients for which any sparse indicator or a particular sparse indicator was detected at each of the one or more data-set units. Such data may be presented in an interactive manner, such that a user may select a represented portion of the data to drill down into that data. For example, the interface may accept a selection of a representation of each data-set unit, and the interface may be updated to identify a distribution of particular sparse indicators detected at the data-set unit.

A drill-down may be configured to, at some level, begin representing non-data set data. For example, a selection of a particular sparse indicator or data-set unit may result in a display identifying a distribution of history data or demographic data from amongst clients associated with the particular sparse indicator or a sparse indicator at the data-set unit. Thus, the drill-down may include retrieving data from different data stores depending on a level of precision. Further, each step in the drill-down may involve evaluating one or more applicable access constraints.

In some instances, a query may pertain to one or more data-set units, and query processing may include retrieving data (or results derived therefrom) and retrieving data set availability data (or results derived therefrom). For example, query processing may include identifying, for each subject and for each of the one or more data-set units, whether a sparse indicator or an data set availability modification was detected. A query result presentation may identify, for example, a portion of subjects for which a sparse indicator or modification was detected for each of the data-set units and/or a query result presentation may identify, for each of the one or more data-set units, a portion of subjects or clients for which a particular type of sparse indicator or modification was detected. The presentation may again be configured to accept drill-down inputs so as to enable a user to further explore the pertinent data.

Figure 6:
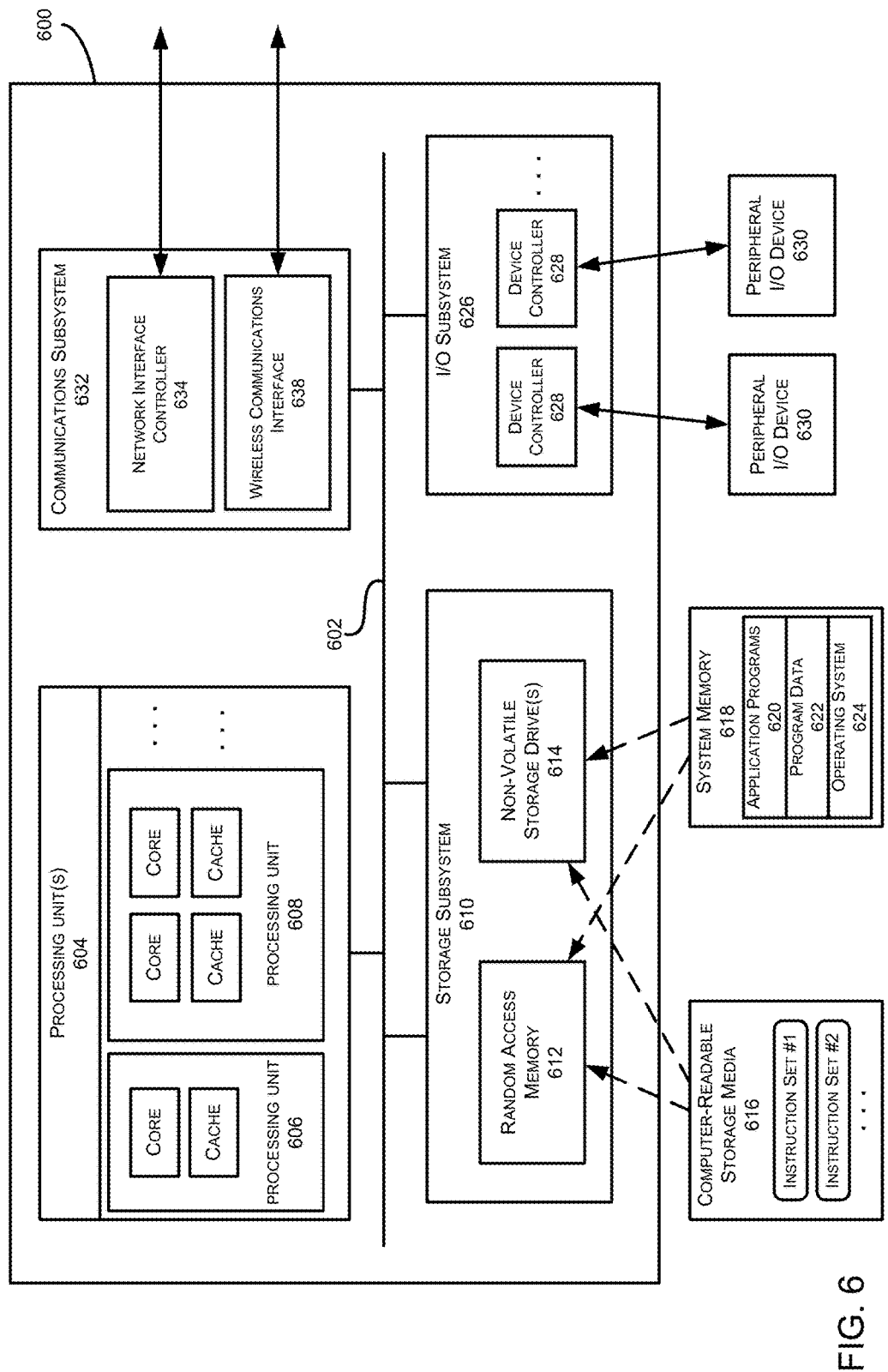
FIG. 6 shows a block diagram of an example data processing network device or system, in accordance with some embodiments.

FIG. 6 illustrates a block diagram of an assessment network device 600. The device 600 may correspond to any of the devices or systems of the assessment network 100 described above, or any other computing devices described herein, and specifically may include, for example, one or several of an assessment system 105, a requestor device 110, a client device 130, a distribution device 135, an assessment device 145, a technician device 150, an access control device 160a, a reviewer device 180, an external assessment device 190, external system 249, data-characterizer device 410, data set analyzer(s) 420, and/or any of the work flow processors 535, 540, 545, 550, and 555. Aspects of device 600 may further be incorporated in one or more data stores 155, 165, 176, 177, 178, 181, 182, 183, 415, 425, and 430 and data store 372. It will be appreciated that each of the devices referred to that may correspond to an instance of device 600 may be independent and unique from all other instances of device 600 and may include fewer or additional components as those illustrated in FIG. 6.

In the example illustrated in FIG. 6, device 600 includes processing units 604 that communicate with a number of peripheral subsystems via a bus subsystem 602. These peripheral subsystems include, for example, a storage subsystem 610, an I/O subsystem 626, and a communications subsystem 632.

Bus Subsystem 602 provides a mechanism for letting the various components and subsystems of device 600 communicate with each other. Although bus subsystem 602 is shown schematically as a single bus, alternative embodiments of the bus subsystem may utilize multiple buses. Bus subsystem 602 may be any of several types of bus structures including a memory bus or memory controller, a peripheral bus, and a local bus using any of a variety of bus architectures. Such architectures may include, for example, an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which may be implemented as a Mezzanine bus manufactured to the IEEE P1386.1 standard.

Processing unit 604, which may be implemented as one or more integrated circuits (e.g., a conventional microprocessor or microcontroller), controls the operation of device 600. Processing unit 604 may be implemented as a special purpose processor, such an application-specific integrated circuit, which may be customized for a particular use and not usable for general-purpose use. One or more processors, including single core and/or multicore processors, may be included in processing unit 604. As shown in FIG. 6, processing unit 604 may be implemented as one or more independent processing units 606 and/or 608 with single or multicore processors and processor caches included in each processing unit. In other embodiments, processing unit 604 may also be implemented as a quad-core processing unit or larger multicore designs (e.g., hexa-core processors, octo-core processors, ten-core processors, or greater).

Processing unit 604 may execute a variety of software processes embodied in program code, and may maintain multiple concurrently executing programs or processes. At any given time, some or all of the program code to be executed may be resident in processor(s) 604 and/or in storage subsystem 610. In some embodiments, device 600 may include one or more specialized processors, such as digital signal processors (DSPs), outboard processors, graphics processors, application-specific processors, and/or the like.

I/O subsystem 626 may include device controllers 628 for one or more user interface input devices and/or user interface output devices 630. User interface input and output devices 630 may be integral with device 600 (e.g., integrated audio/video systems, and/or touchscreen displays), or may be separate peripheral devices which are attachable/detachable from device 600. The I/O subsystem 626 may provide one or several outputs to a user by converting one or several electrical signals to user perceptible and/or interpretable form, and may receive one or several inputs from the user by generating one or several electrical signals based on one or several user-caused interactions with the I/O subsystem such as the depressing of a key or button, the moving of a mouse, the interaction with a touchscreen or trackpad, the interaction of a sound wave with a microphone, or the like.

Input devices 630 may include a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. Input devices 630 may also include three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, haptic devices, and eye gaze tracking devices. Additional input devices 630 may include, for example, motion sensing and/or gesture recognition devices that enable users to control and interact with an input device through a natural user interface using gestures and spoken commands, eye gesture recognition devices that detect eye activity from users and transform the eye gestures as input into an input device, voice recognition sensing devices that enable users to interact with voice recognition systems through voice commands, medical imaging input devices, MIDI keyboards, digital musical instruments, and the like.

Output devices 630 may include one or more display subsystems, indicator lights, or non-visual displays such as audio output devices, etc. Display subsystems may include, for example, cathode ray tube (CRT) displays, flat-panel devices, such as those using a liquid crystal display (LCD) or plasma display, light-emitting diode (LED) displays, projection devices, touch screens, haptic devices, and the like. In general, use of the term "output device" is intended to include all possible types of devices and mechanisms for outputting information from device 600 to a user or other computer. For example, output devices 630 may include, without limitation, a variety of display devices that visually convey text, graphics and audio/video information such as monitors, printers, speakers, headphones, automotive navigation systems, plotters, voice output devices, and modems.

Device 600 may comprise one or more storage subsystems 610, comprising hardware and software components used for storing data and program instructions, such as system memory 618 and computer-readable storage media 616. The system memory 618 and/or computer-readable storage media 616 may store program instructions that are loadable and executable on processing units 604, as well as data generated during the execution of these programs. Program instructions may include instructions to perform one or more actions or part(s) or all of one or more methods or processes described herein. For example, program instructions may include instructions for identifying and/or aligning sparse indicators. Program instructions may include instructions for generating, transmitting, and/or receiving communications. Program instructions may include instructions for automated processing. Program instructions may include instructions for generating automated processing and/or stage results. Program instructions may include instructions for performing a work flow iteration.

Depending on the configuration and type of device 600, system memory 618 may be stored in volatile memory (such as random access memory (RAM) 512) and/or in non-volatile storage drives 614 (such as read-only memory (ROM), flash memory, etc.) The RAM 612 may contain data and/or program modules that are immediately accessible to and/or presently being operated and executed by processing units 604. In some implementations, system memory 618 may include multiple different types of memory; such as static random access memory (SRAM) or dynamic random access memory (DRAM). In some implementations, a basic input/output system (BIOS), containing the basic routines that help to transfer information between elements within device 600, such as during start-up, may typically be stored in the non-volatile storage drives 614. By way of example, and not limitation, system memory 618 may include application programs 620, such as user applications, Web browsers, mid-tier applications, server applications, etc., program data 622, and an operating system 624.

Storage subsystem 610 also may provide one or more tangible computer-readable storage media 616 for storing the basic programming and data constructs that provide the functionality of some embodiments. Software (programs, code modules, instructions) that when executed by a processor provide the functionality described herein may be stored in storage subsystem 610. These software modules or instructions may be executed by processing units 604. Storage subsystem 610 may also provide a repository for storing data used in accordance with the present invention.

Storage subsystem 610 may also include a computer-readable storage media reader that may further be connected to computer-readable storage media 616. Together and, optionally, in combination with system memory 618, computer-readable storage media 616 may comprehensively represent remote, local, fixed, and/or removable storage devices plus storage media for temporarily and/or more permanently containing, storing, transmitting, and retrieving computer-readable information.

Computer-readable storage media 616 containing program code, or portions of program code, may include any appropriate media known or used in the art, including storage media and communication media, such as but not limited to, volatile and non-volatile, removable and non-removable media implemented in any method or technology for storage and/or transmission of information. This may include tangible computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media. This may also include nontangible computer-readable media, such as data signals, data transmissions, or any other medium that may be used to transmit the desired information and that may be accessed by device 600.

By way of example, computer-readable storage media 616 may include a hard disk drive that reads from or writes to non-removable, nonvolatile magnetic media, a magnetic disk drive that reads from or writes to a removable, non-volatile magnetic disk, and an optical disk drive that reads from or writes to a removable, nonvolatile optical disk such as a CD ROM, DVD, and Blu-Ray disk, or other optical media. Computer-readable storage media 616 may include, but is not limited to, Zip drives, flash memory cards, universal serial bus (USB) flash drives, secure digital (SD) cards, DVD disks, digital video tape, and the like. Computer-readable storage media 616 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for device 600.

Communications subsystem 632 may provide a communication interface from device 600 and remote computing devices via one or more communication networks, including local area networks (LANs), wide area networks (WANs) (e.g., the Internet), and various wireless telecommunications networks. As illustrated in FIG. 6, the communications subsystem 632 may include, for example, one or more network interface controllers (NICs) 634, such as Ethernet cards, Asynchronous Transfer Mode NICs, Token Ring NICs, and the like, as well as one or more wireless communications interfaces 638, such as wireless network interface controllers (WNICs), wireless network adapters, and the like. Additionally and/or alternatively, the communications subsystem 632 may include one or more modems (telephone, satellite, cable, ISDN), synchronous or asynchronous digital subscriber line (DSL) units, FireWire interfaces, USB interfaces, and the like. Communications subsystem 632 also may include radio frequency (RF) transceiver components for accessing wireless voice and/or data networks (e.g., using cellular telephone technology, advanced data network technology, such as 3G, 4G or EDGE (enhanced data rates for global evolution), Wi-Fi (IEEE 802.11 family standards, or other mobile communication technologies, or any combination thereof), global positioning system (GPS) receiver components, and/or other components.

The various physical components of the communications subsystem 632 may be detachable components coupled to the device 600 via a computer network, a FireWire bus, a serial bus, or the like, and/or may be physically integrated onto a motherboard or circuit board of device 600. Communications subsystem 632 also may be implemented in whole or in part by software.

In some embodiments, communications subsystem 632 may also receive input communication in the form of structured and/or unstructured data feeds, event streams, event updates, and the like, on behalf of one or more users who may use or access device 600. For example, communications subsystem 632 may be configured to receive data feeds in real-time from other communication services, web feeds such as Rich Site Summary (RSS) feeds, and/or real-time updates from one or more third party information sources. Additionally, communications subsystem 632 may be configured to receive data in the form of continuous data streams, which may include event streams of real-time events and/or event updates (e.g., data set completion, results transmission, other data transmission, report transmission, etc.). Communications subsystem 632 may output such structured and/or unstructured data feeds, event streams, event updates, and the like to one or more data stores that may be in communication with device 600.

Due to the ever-changing nature of computers and networks, the description of device 600 depicted in FIG. 6 is intended only as a specific example. Many other configurations having more or fewer components than the device depicted in the figure are possible. For example, customized hardware might also be used and/or particular elements might be implemented in hardware, firmware, software, or a combination. Further, connection to other computing devices, such as network input/output devices, may be employed. Based on the disclosure and teachings provided herein, it will be appreciated that there are other ways and/or methods to implement the various embodiments.

Figure 7:
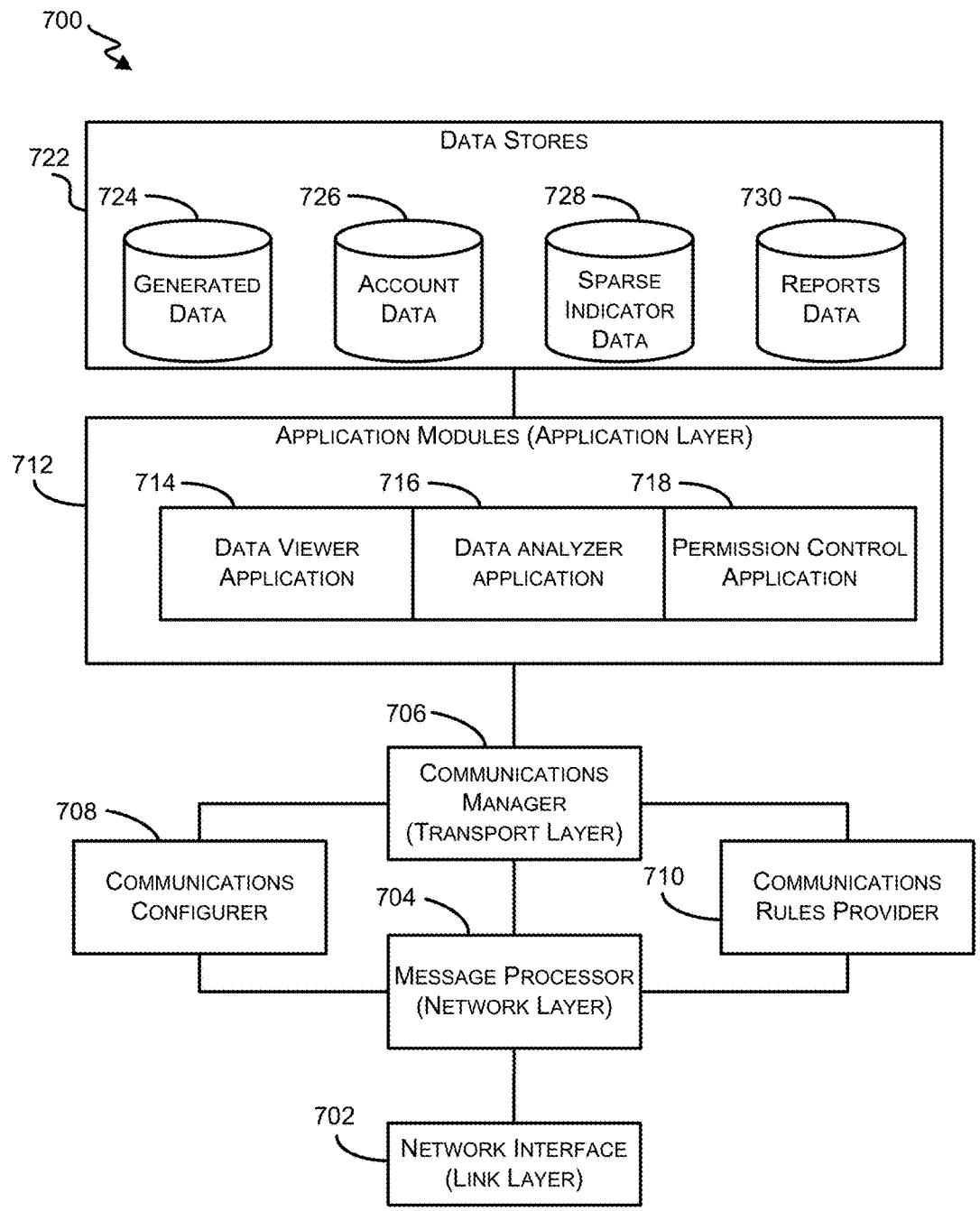
FIG. 7 illustrates components of a data processing network device or system, in accordance with some embodiments.

FIG. 7 illustrates a diagram of components of an assessment network device 700. The device 700 may correspond to any of the devices or systems of the assessment network 100 described above, or any other computing devices described herein, and specifically may include, for example, one or several of an assessment system 105, a requestor device 110, a client device 130, a distribution device 135, an assessment device 145, a technician device 150, an access control device 160a, a reviewer device 180, an external assessment device 190, external system 249, data-characterizer device 410, data set analyzer 420, any of the work flow processors 535, 540, 545, 550, and 555, and/or device 600. Aspects of device 700 may further be incorporated in one or more of data stores 155, 165, 176, 177, 178, 181, 182, 183, 415, 425, and 430, and data store 372. It will be appreciated that each of the devices referred to that may correspond to an instance of device 700 may be independent and unique from all other instances of device 700 and may include fewer or additional components as those illustrated in FIG. 7.

Various components may be included in device 700. Components may include some or all of the following: a network interface 702 (which may operate in or function as a link layer of a protocol stack), a message processor 704 (which may operate in or function as a network layer of a protocol stack), a communications manager 706 (which may operate in or function as a transport layer of a protocol stack), a communications configurer 708 (which may operate in or function as a portion of transport and/or network layer in a protocol stack), a communications rules provider 710 (which may operate in or function as part of a transport and/or network layer in a protocol stack), and applications 712 (which may operate in or function as an application layer of a protocol stack).

Network interface 702 receives and transmits messages via one or more hardware components that provide a link-layer interconnect. The hardware components associated with network interface 702 may include, for example, a radio frequency (RF) antenna or a port (e.g., Ethernet port) and supporting circuitry. In some embodiments, network interface 702 may be configured to support wireless communication, e.g., using Wi-Fi (IEEE 802.11 family standards), Bluetooth, or other wireless communications standards.

The RF antenna, if present, may be configured to convert electric signals into radio and/or magnetic signals (e.g., to radio waves) to transmit to another device and/or to receive radio and/or magnetic signals and convert them to electric signals. RF antenna may be tuned to operate within a particular frequency band. In some instances, device 700 includes multiple antennas, and the antennas may be, for example, physically separated. In some instances, antennas differ with respect to radiation patterns, polarizations, take-off angle gain and/or tuning bands. Network interface 702 may include one or more phase shifters, filters, attenuators, amplifiers, switches and/or other components to demodulate received signals, coordinate signal transmission and/or facilitate high-quality signal transmission and receipt using the RF antenna.

In some instances, network interface 702 includes a virtual network interface, so as to enable the device to utilize an intermediate device for signal transmission or reception. For example, network interface 702 may include or utilize virtual private networking (VPN) software.

Network interface 702 may be configured to transmit and receive signals over one or more connection types. For example, network interface may be configured to transmit and receive Wi-Fi signals, Ethernet signals, cellular signals, Bluetooth signals, etc.

Message processor 704 may coordinate communication with other electronic devices or systems, such as one or more user devices, requestor devices, assessment systems, data stores, assessment devices, distribution device, reviewer device, etc. In one instance, message processor 704 is able to communicate using a plurality of protocols (e.g., any known, future and/or convenient protocol such as, but not limited to, internet protocol (IP), short message service, (SMS), multimedia message service (MMS), etc.). Message processor 704 may further optionally serialize incoming and/or outgoing messages and facilitate queuing of incoming and outgoing message traffic.

Message processor 704 may perform functions of an Internet or network layer in a network protocol stack. For example, in some instances, message processor 704 may format data packets or segments, combine data packet fragments, fragment data packets and/or identify destination applications and/or device addresses. For example, message processor 704 may defragment and analyze an incoming message to determine whether it is to be forwarded to another device and, if so, may address and fragment the message before sending it to the network interface 702 to be transmitted. As another example, message processor 704 may defragment and analyze an incoming message to identify a destination application that is to receive the message and may then direct the message (e.g., via a transport layer) to the application.

Communications manager 706 may implement transport-layer functions. For example, communications manager 706 may identify a transport protocol for an outgoing message (e.g., transmission control protocol (TCP) or user diagram protocol (UDP)) and appropriately encapsulate the message into transport protocol data units. Message processor 704 may initiate establishment of connections between devices, monitor transmissions failures, control data transmission rates, and monitor transmission quality. As another example, communications manager 706 may read a header of an incoming message to identify an application layer protocol used to receive the message's data. The data may be separated from the header and sent to the appropriate application. Message processor 704 may also monitor the quality of incoming messages, detect out of order incoming packets, detect missing packets, reorder out of order packets, request retransmission of missing packets, request retransmission of out of order packets, etc.

In some instances, characteristics of message-receipt or message-transmission quality may be used to identify a quality status of an established communications link. In some instances, communications manager 706 may be configured to detect signals indicating the stability of an established communications link (e.g., a periodic signal from the other device system, which if received without dropouts, indicates a stable link).

In some instances, a communication configurer 708 is provided to track attributes of another system so as to facilitate establishment of a communication session. In one embodiment, communication configurer 708 further ensures that inter-device communications are conducted in accordance with the identified communication attributes and/or rules. Communication configurer 708 may maintain an updated record of the communication attributes of one or more devices or systems. In one embodiment, communications configurer 708 ensures that communications manager 706 may deliver the payload provided by message processor 704 to the destination (e.g., by ensuring that the correct protocol corresponding to the receiving system is used). Optionally, communications configurer 708 may reformat, encapsulate, or otherwise modify the messages directed to the message processor 704 to ensure that the message processor 704 is able to adequately facilitate transmission of the messages to their ultimate destination.

A communications rules provider 710 may implement one or more communication rules that relate to details of signal transmissions or receipt. For example, a rule may specify or constrain a protocol to be used, a transmission time, a type of link or connection to be used, a destination device, and/or a number of destination devices. A rule may be generally applicable or conditionally applicable (e.g., only applying for messages corresponding to a particular app, during a particular time of day, while a device is in a particular geographical region, when a usage of a local device resource exceeds a threshold, etc.). For example, a rule may identify a technique for selecting between a set of potential destination devices based on attributes of the set of potential destination devices as tracked by communication configure 708. To illustrate, a device having a short response latency may be selected as a destination device. As another example, communications rules provider 710 may maintain associations between various devices or systems and resources. Thus, messages corresponding to particular resources may be selectively transmitted to destinations having access to such resources.

A variety of applications 712 may be configured to initiate message transmission, process incoming transmissions, facilitate permissions requests for access to protected data, facilitate automatic access to protected data, facilitate task work flow permission verification, and/or performing other functions. In the instance depicted in FIG. 7, application modules 712 include a data viewer application 714, a data analyzer application 716, and/or a permission control application 718. It will be appreciated that the application modules depicted in FIG. 7 are merely examples and other example application modules are include, but are not limited to, one that is associated with aspects of part or all of each of one or more actions, methods, and/or processes disclosed herein.

Data stores 722 may store data for use by application modules 712, as necessary, and may include, for example, generated data store 724, account data store 726, sparse indicator data store 728, and reports data store 730. Optionally, data store 372 may be included in data stores 722. It will be appreciated that fewer or more or different data stores than those illustrated in FIG. 7 may be included in data stores 722, such as any one or more of data stores 155, 165, 176, 177, 178, 181, 182, and 183 depicted in FIG. 1.

One or more of data stores 724, 726, 728, and 730 may be a relational data store, such that elements in one data store may be referenced within another data store. For example, account data store 726 may associate an identifier of a particular account with an identifier of a particular user or client. Additional information about the user may then be retrieved by looking up the account identifier in sparse indicator data store 728, for example.

The components illustrated in FIG. 7 may be useful for establishing data communications and exchanging data between various other systems. For example, independent instances of device 700 may represent the requestor device 110 and the assessment system 105 illustrated in FIGS. 1 and 2. Other examples are possible.

As an example, data analyzer application 716 may perform alignment of data sets, request reference data, determine sparse indicators, determine scores, determine buckets, etc. Such actions may be performed in response to messages received by device 700 from another instance of device 700. If data that is unavailable locally in device 700 is needed by an application module 712, a request may be transmitted by device 700, first by generating the request, forwarding the request to communications manager 706, which then may process and modify the request as necessary for subsequent handling by message processor 704. In turn, message processor 704 may process and modify the request as necessary, such as by adding header and/or footer information, for subsequent handling by network interface 702. Network interface 702 may then perform further processing and modification of the request, such as by adding additional header and/or footer information, and then facilitate transmission of the request to a remote system, such as an external system that may possess the needed data.

Figure 8:
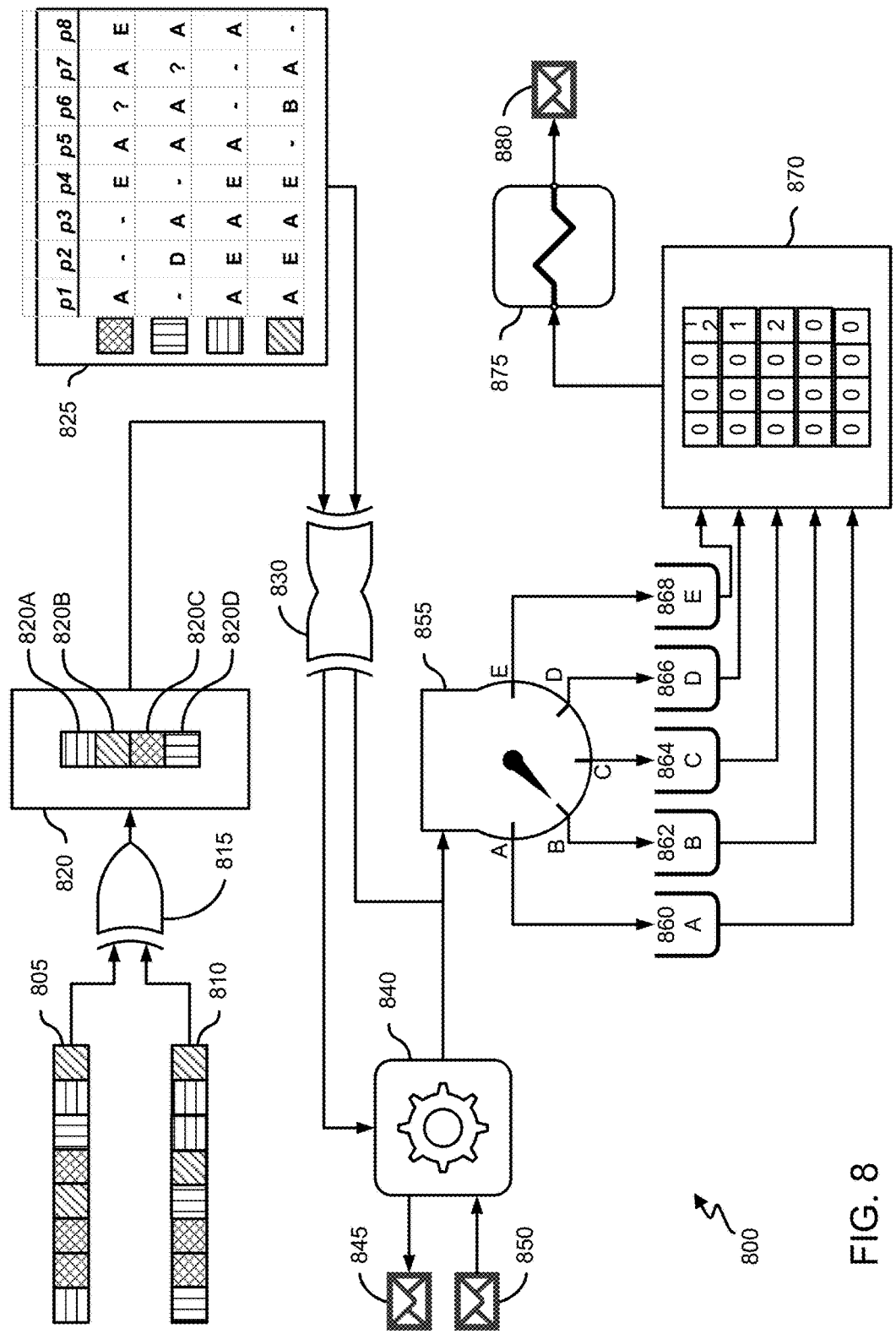
FIG. 8 shows a representation of a system for generating communications, in accordance with some embodiments.

Referring next to FIG. 8, a representation of a system 800 for assigning sparse indicators to data buckets is shown, such as by performing a work flow iteration(s), performing automated processing for stage(s), generating stage result(s) from one or more stages of a work flow, and analyzing data buckets. System 800 may represent portions of assessment system 105 and may, for example, include portions of data generator 140. System 800 may be in data communication with one or more other components of assessment network 100 or 300, such as client device 130 and data store 372, for example.

System 800 includes an assessment device 815, which may be used to analyze and/or compare generated data 805 with reference data 810 to generate a data stream 820, which may include one or more sparse indicators 820A, 820B, 820C, 820D, etc. Thus, it will be appreciated that data 805 may include data aligned with a portion of a reference set, such that individual values of data 805 may be compared to corresponding values in reference data 810. In some embodiments, multiple individual data sets are obtained for a particular client and a compiled data set may be assembled from alignments of a plurality of the individual data sets. The compiled data set may be compared with one or more reference data sets or a compiled reference data set to identify sparse indicators associated with the compiled data set for the particular client. It will also be appreciated that generated data 805 may include identifier data and coverage data that may be used by assessment device 815 in generating data stream 820, such as by comparing identifier data with reference data 810 and using coverage data in tandem to determine a type, identity, value, and/or confidence metric associated with a sparse indicator in data stream 820.

Different types of sparse indicators may be identified, such as a one-element sparse indicator representing a single data element different from a reference data set, or a clustered sparse indicator representing a set of consecutive data elements different from a reference data set. A clustered sparse indicator may be detected upon determining (for example) that a series of elements in a data set generally differ from those in a reference data set or that values in a coverage set change across the set so as to indicate that a portion of the reference data set is over- or underrepresented in the data set. Thus, in some instances, a reference set may include a reference coverage set. Although only four sparse indicators 820A-820D are depicted as part of data stream 820, it will be appreciated that more or fewer sparse indicators may be identified for a particular set of generated data and that the four sparse indicators 820A-820D are merely examples.

System 800 further includes a look-up engine 830, which may determine whether each individual sparse indicator corresponds to bucket-assignment data in stored data 825 (e.g., a look-up table). For example, a look-up table may include a set of entries, each of which corresponds to a sparse indicator. A sparse indicator may be identified (for example) by a position and identifier or by a range of positions and type of sparse identifier (e.g., type of structural sparse identifier and/or one or more corresponding position ranges in a reference data set). For example, FIG. 8 illustrates stored data 825 arranged in a table or array, such that a value along a first dimension can represent an identifier detected in a client data set and a value along a second dimension can represent a position at which the identifier was detected. Elements that correspond to those in a reference data set need not have a value. Each of one or more other elements may include bucket-assignment data, which may identify a bucket to which the sparse indicator is to be assigned and, in some instances, a confidence of such assignment. In some instances, one or more elements indicate that bucket-assignment data is not yet available).

The depicted stored data 825 may be useful for identifying bucket-assignment data for sparse indicators corresponding to differences between a client data set and reference data set at individual positions. It will be appreciated that additional stored data 825 may identify bucket-assignment for other types of sparse indicators (e.g., structural sparse indicators), such as a sparse indicator that indicates that elements from Position X to Position Y are not present in a client data set.

If a look-up of a particular sparse indicator is successful, look-up engine 830 may proceed to assign the sparse indicator in accordance with the bucket-assignment data. If a look-up of the particular sparse indicator is not successful or if a work flow calls for additional stages, the information associated with the sparse indicator and/or the result(s) from the look-up may be directed to data processor 840.

Look-up engine 830 may further allow for filtering of sparse indicators, such as to determine when a reviewer-assisted analysis of a particular sparse indicator is not needed or not to be performed. For example, some sparse indicators may be pre-assigned to particular data bucket(s) and look-up engine may identify these sparse indicators as such. In another example, some sparse indicators may not be suitable for an iterative analysis and/or may predetermined such that no resources are to be used in analyzing the sparse indicator. For example, some sparse indicators are associated with a position in a full data set for which analysis is determined to be unnecessary. Optionally, some sparse indicators are associated with a position in a full data set and value for which analysis is determined to be unnecessary.

System 800 further includes a data processor 840, which may perform iterative performance of automated processing for each of the sparse indicators in data stream 820. It will be appreciated that more data processors 840 may be included in system 800, such as to allow parallel and/or sequential work flow performance. Data processor 840 may perform fully automated processing of stages of a work flow and forward stage result(s) to bucketor 855 for data bucket assignment.

In some embodiments of automated processing for one or more sparse indicators, data processor 840 may encounter one or more stages having a stage-progression condition that is not satisfied or may determine that a reviewer-engagement condition is satisfied (e.g., due to a failure to identify a bucket for a sparse indicator in a look-up data store or due to determining that a bucket assignment for a sparse indicator is associated with a confidence metric that is below a predefined quantitative or qualitative threshold). Optionally, data processor 840 may generate and transmit a query communication 845 that includes one or more of a position associated with a sparse indicator, one or more values associated with the sparse indicator, and a result(s) from a previous stage of the work flow. The query communication 845 may be transmitted, for example, from system 800 to an evaluation device 170 to facilitate review and/or input by evaluator 175. For example, evaluation device 170 may receive the query communication 845 and display the included information to allow the evaluator 175 to provide response data to satisfy the stage-progression condition. Evaluation device 170 may then generate a response communication 850 that includes response data. Data processor 840 may receive response communication 850 and use the included response data to complete or augment the automated processing to generate stage result(s). Once the stages are completed according to the work flow, stage result(s) may be forward to bucketor 855.

System 800 further includes bucketor 855, which may assign each sparse indicator to a bucket of a plurality of data buckets, such as by using stage result(s) from data processor 840 and/or look-up result(s) from look-up engine 830. Bucketor 855 may then assign a particular data bucket for the particular sparse indicator being analyzed. It will be appreciated that more bucketors 855 may be included in system 800. In system 800, five data buckets 860, 862, 864, 866, and 868 are depicted, though it will be appreciated that more or fewer data buckets may be utilized. Some or all of data buckets 860-868 may, for example, span a range along a spectrum of a degree of likeliness that a client will transition into or experience a particular state. Upon full or partial completion of the assignment of the sparse indicators in data stream 820 to data buckets, information may be passed to bucket assessor 870. It will be appreciated that counts assigned to a set of buckets may be determined with respect to each of multiple position ranges (or units) or combinations thereof. For example, for a given data set, a count may be generated for each of a set of buckets and for each of a set of units that reflects a number of sparse indicators detected for the unit that correspond to the bucket.

System 800 further includes bucket assessor 870. Although bucket assessor 870 is shown schematically as a separate component from bucketor 855, it will be appreciated that bucket assessor 870 and bucketor 855 may be combined in a single component or process. Bucket assessor 870 may identify a number of sparse indicators assigned to particular buckets 860-868 using one or more counters, for example. Bucket assessor 870 may optionally determine whether one or more buckets include counts above a predetermined threshold (e.g., whether a count exceeds zero). The predetermined threshold may be (for example) defined by a user, generated based on machine learning, generated based on a virtual structural representor, and/or generated based on a population analysis. For example, in one instance, it may be determined whether a count in a given bucket or a total count across a combination of buckets (e.g., a bucket corresponding to a highest predicted likelihood, amongst the buckets, of transitioning into or being in a particular state or two buckets corresponding to the two highest predicted likelihoods) exceeds zero. It will be appreciated that predetermined thresholds for each data bucket may be independent of other predetermined thresholds. Bucket assessor 870 may forward the counts corresponding to the buckets 860-868 to signal generator 875.

A signal generator may use the counts and/or results of a threshold comparison, for example, to generate a communication 880 indicative of whether a number of sparse indicators assigned to particular data buckets exceed the predetermined threshold(s). In some embodiments, different templates for communication 880 may be used depending on which data bucket(s) exceed the predetermined threshold(s) and or by how much a threshold(s) is exceeded, for example. Communication 880 may identify, for example, whether one or more sparse indicators are assigned to a bucket representing a highest probability, amongst the buckets, of transitioning into or being at a particular state. Communication 880 may identify, for example, whether one or more sparse indicators are assigned to each of one or more other buckets.

Figure 9:
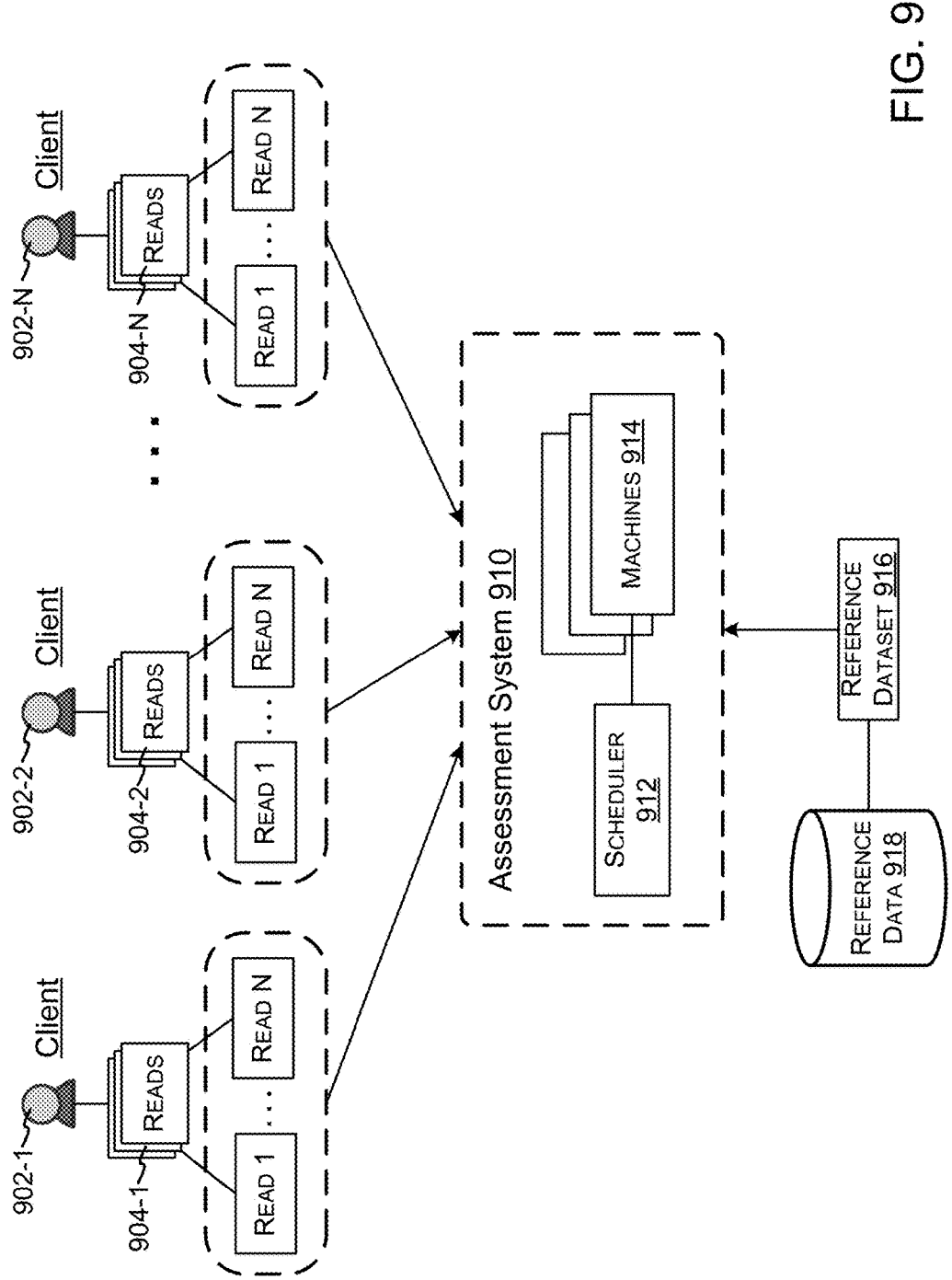
FIG. 9 illustrates a system diagram for distributing assignment tasks in accordance with embodiments in the present disclosure.

FIG. 9 illustrates a system diagram for distributing assignment tasks in accordance with embodiments in the present disclosure. It should be noted that FIG. 9 includes some components and struture to the system shown in FIG. 4, and tasks can be divided among the machines 914 similarly to how tasks can be divided among the analyzers 420.

More specifically, in FIG. 9, there may be a plurality of clients 902-1 through 902-N. Each of the clients 902-1 through 902-N may be associated with a set of reads, such as the sets of reads 904-1 through 904-N. A set of reads associated with a client may have any number of individual reads, although in practice there may be thousands of individual reads in the set of reads associated with the client.

As previously mentioned, the set of reads associated with a client may be obtained from a data generation system, which may process a client's sample to generate the set of reads. In some cases, the set of reads associated with a client's sample may even come from more than one data generation systems.

The sets of reads 904-1 through 904-N may be sent (e.g., from the data generation systems) to the assessment system 910 over time. The assessment system 910 may include a scheduler 912 and a plurality of machines 914. The scheduler 912 may be configured to distribute various tasks among the machines 914. In some embodiments, the scheduler 912 may distribute tasks among the machines 914 in order to balance the resource utilization across the machines 914. For example, tasks may be divided based on a type of task, a client, and/or a data dependency. In some instances, a same type of task is to be performed with respect to different data segments (e.g., different reads and/or different portions of a reference data set) associated with a same client, and the data segments may be distributed across two or more machines to perform the task.

One example of a task that may be distributed across the machines 914 is the alignment of reads. In some embodiments, each of the machines 914 may be responsible for performing alignments of reads against the entire reference dataset 916 taken from the reference data store 918. For instance, a machine tasked with aligning a read for a client may determine multiple portions in the entire reference dataset 916 to which part of, or all of, the read aligns.

In some embodiments, each of the machines 914 may be responsible for performing alignments of reads against just a part of the reference dataset 916. For instance, a machine tasked with aligning a read for a client may determine multiple portions in the part of the reference dataset 916 assigned to that machine that the read aligns with. The multiple portions may, but need not, be overlapping.

In some embodiments, one of the machines 914 may be tasked with performing an alignment for all of the reads associated with a client. For example, all of the reads in the set of reads 904-1 associated with client 902-1 could be sent to a single machine to perform alignment.

In some embodiments, the set of reads associated with a specific client may be distributed across multiple computers in order for an alignment to be performed. For example, the reads in the set of reads 904-1 associated with client 902-1 could be distributed among various machines 914 by the scheduler 912. Thus, one machine could perform an alignment task on some of the reads associated with client 902-1, while another machine performs an alignment task on other reads associated with client 902-1.

Accordingly, in various embodiments, the distribution of alignment tasks across machines 914 can be done in two dimensions (e.g., the reference dataset 916 can be broken up, or the set of reads associated with a client can be broken up). For example, each of the machines 914 may be tasked with performing all the alignments associated with a particular client across the entire reference dataset 916, such that a machine would receive all of the reads associated with a client and align those reads against the entire reference dataset 916. Alternatively, each of the machines 914 may be tasked with performing alignments using a different section or part of the reference dataset 916. Each of the machines 914 would receive the same read, for the same client, and would have to align that read against the part of the reference dataset 916 assigned to that machine. Since each of the machines 914 that are assigned a different portion of the reference dataset 916, the alignment results for a read from all of the machines 914 can be combined (as part of a step referred to as "post-processing"). This would allow the alignment results against the entire reference dataset 916 for the read to be stitched together instead of having a single machine performing alignments on that read against the entire reference dataset 916—except the process could be faster and more efficient since it is distributed across multiple machines 914.

In some embodiments, a read alignment may not be a binary characterization (e.g., aligned/not aligned). In other words, a read may not perfectly align with a corresponding portion of the reference dataset 916. Instead, the alignment task may involve generating various alignment scores associated with the read which represent a score of how well the read is aligned to corresponding portions of the reference dataset 916. There may be a threshold for the alignment score, such that the read is considered aligned to any portions of the reference dataset 916 having alignment scores above that threshold.

In some embodiments, each of the machines 914 may perform their alignment tasks based on the alignment score threshold, such that each of the machines 914 reports on the portions of the reference dataset 916 (or the sections of the reference dataset 916 assigned to that machine) that have an alignment score above the threshold for the read. For instance, if each of the machines 914 is tasked with performing an alignment of the same read using a different section of the reference dataset 916, each machine may produce an alignment result indicating which portions of the section of the reference dataset 916 assigned to that machine have an alignment score above the threshold. The alignment scores associated with those portions may also be indicated. In other embodiments, each of the machines 914 may only report on the portion of the reference dataset 916 (or the portions of section of the reference dataset 916 assigned to that machine) that has the best alignment score. Both of these approaches are described in FIG. 10.

It should also be noted that, as previously described, each of the machines 914 may receive data for reads over a period of time. In various instances, the reads from the data generator systems may be transmitted to assessment system 105 in a batch-mode, in a streaming mode, in real-time as data is produced, and/or upon request. A given transmission or stream may include data that corresponds to a single, or in other instances to multiple, client, sample, and/or data reads. Thus, the data for reads may come in slowly over time or in batches, and the reads may be distributed among the machines 914 for alignment as they come in.

Figure 10:
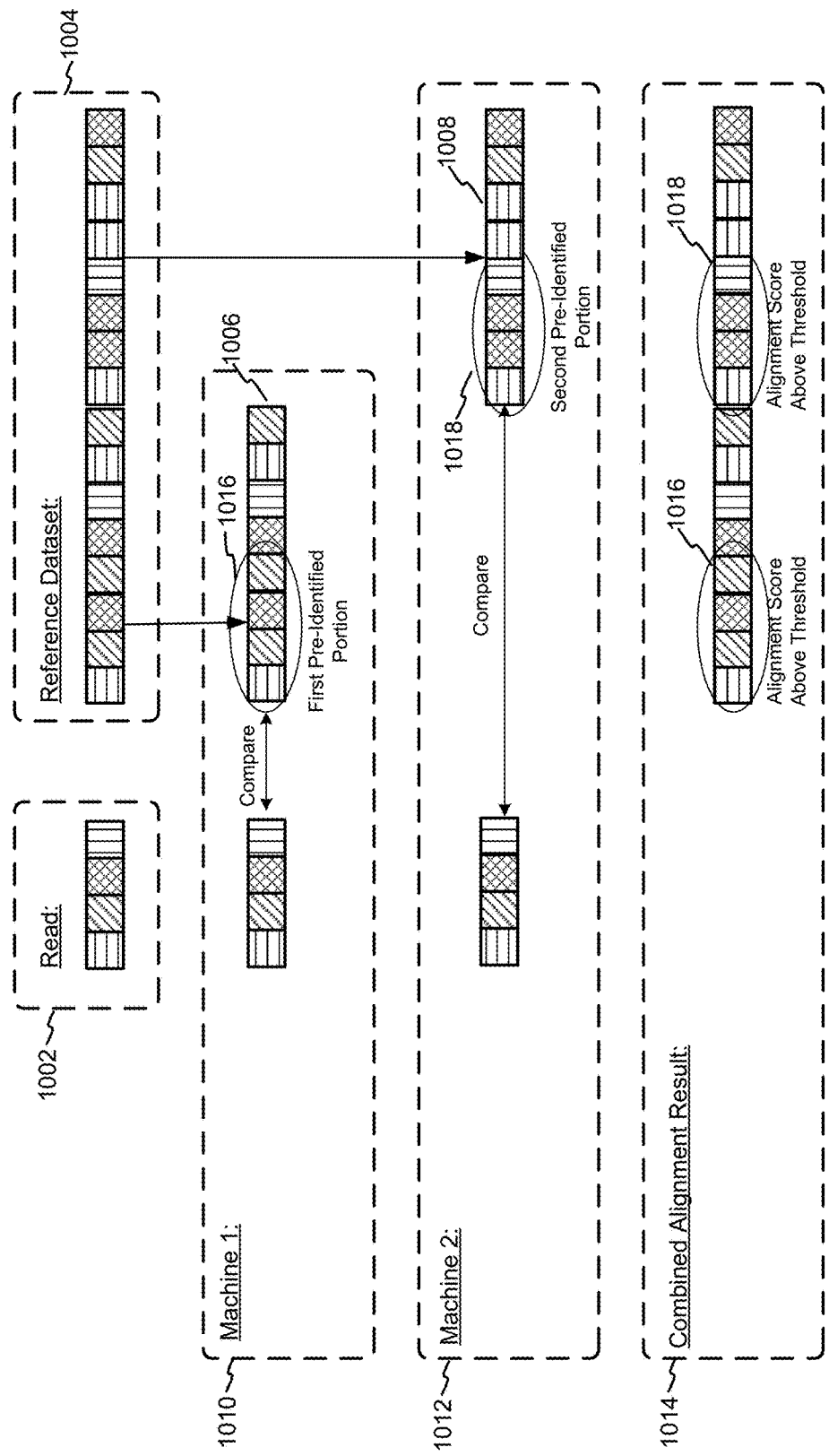
FIG. 10 illustrates a process for distributing assignment tasks in accordance with embodiments of the present disclosure.

FIG. 10 illustrates a process for distributing assignment tasks in accordance with embodiments of the present disclosure.

An example depiction of a read 1002 is shown along with an entire reference dataset 1004. In practice, the read 1002 or the reference dataset 1004 may be much larger. In some instances, distributed processing is configured (e.g., via a scheduler) to assign—to each of the set of machines—tasks associated with a particular portion of the reference dataset 1004. For example, the reference dataset 1004 can be conceptually broken into two separate parts, a first part 1006 and a second part 1008 (e.g., each defined by a start index, end index and/or length), which can be distributed among separate machines for consideration. In practice, there may be many parts of the reference dataset 1004 (e.g., if there are many machines). In this figure, the first part 1006 is assigned to a first machine 1010 and the second part 1008 is assigned to a second machine 1012.

Both the first machine 1010 and the second machine 1012 may be provided a set of reads, and each machine may be tasked with performing an alignment process on each read in the set of reads provided to that machine. However, in order to better facilitate understanding, only read 1002 is depicted in the figure and the read 1002 has eight identifiers. The reference dataset 1004 is depicted with sixteen identifiers.

To perform the alignment process, the first machine 1010 may perform an alignment process using the read 1002 and the reference dataset 1004 (or the first part 1006 of the reference dataset 1004) in order to generate an alignment result, which may identify one or more portions of the reference dataset 1004 to which the read 1002 is to be aligned. In some embodiments, the first machine 1010 may identify a first pre-identified portion 1016 of the reference dataset 1004. This first pre-identified portion 1016 may be related to a second pre-identified portion 1018 (e.g., a pseudogene) of the reference dataset 1004. A predefined rule may identify the first and second pre-identified portions of being associated with one or more processing exceptions, such as an exception to perform alignment and/or downstream processing in a manner that uses different stringencies. The first pre-identified portion 1016 may have a plurality of positions associated with it. For example, the first pre-identified portion 1016 has four positions represented by four identifiers. In some embodiments, the entire reference dataset 1004 may be considered by a machine, while in other embodiments a machine may consider only part of the entire reference dataset 1004.

The alignment process can include comparing the read 1002 against each of one or more portions (of consecutive positions) of the first part 1006 of the reference dataset 1004. Each portion of the first part 1006 being compared may be associated with an alignment score that represents a degree of correspondence between the read 1002 and the portion. For example, the four identifiers of the read 1002 may be compared against each of the five different contiguous groups of four identifiers in the first part 1006 to generate five scores. A score associated with a first alignment (with the left-most identifier of reach 1002 aligning with the left-most identifier of the first part 1006 of the reference dataset) may be higher than the other four scores given the high degree of identifier correspondence.

It will be appreciated that, depending on the circumstance, an alignment protocol may require that an alignment result identify only one alignment, or—in other instances—multiple alignments may be permitted (e.g., if multiple alignments are associated with an above-threshold score). When different potential alignments of a single read are evaluated using different machines, a variety of evaluation results may be returned. For example, each machine may identify a score (e.g., and partial definition of the corresponding potential alignment) of each potential alignment evaluated. As another example, each machine may identify only a top score (e.g., and partial definition of the corresponding potential alignment). As yet another example, each machine may identify each potential alignment associated with an above-threshold score.

In some embodiments, the alignment score may represent a number, or portion, of matching identifiers between the identifiers of read 1002 and the identifiers of the first part 1006 to which a comparison is being made. For example, for the first pre-identified portion 1016, three of the first four identifiers of read 1002 match the four identifiers of the first alignment portion 1016. Thus, the alignment score for the first alignment portion 1016 may reflect that either three identifiers, or three out of four identifiers, match. This alignment score is likely to be the highest among sets of consecutive identifiers in the first part 1006, since it can be seen that the other sets of four consecutive identifiers in first part 1006 do not have as high of a degree of correspondence to the first four identifiers of read 1002. It will be appreciated that, in some instances, there may be different degrees of matching rather than just a binary result. For example, a first identifier may potentially correspond with a second identifier (e.g., a vice-versa), but neither may correspond with a third identifier or fourth identifier. Similarly, the third identifier may potentially correspond with the fourth identifier (e.g., a vice-versa), but neither may correspond with the first identifier or second identifier. An alignment score may reflect these relationships.

In some embodiments, the alignment score may represent a maximum length of consecutive matching identifiers between the identifiers of read 1002 and the identifiers of the first part 1006 to which a comparison is being made. For example, there is a match between three consecutive identifiers in read 1002 and the first three consecutive identifiers in the first part 1006. Thus, the alignment score may reflect that three consecutive identifiers match. This alignment score is likely to be the highest among sets of consecutive identifiers in the first part 1006.

In some embodiments, once it is determined that an alignment score above a threshold is associated with a specific pre-identified portion of the reference dataset (e.g., the first pre-identified portion 1016), the assessment system may then be directed to perform an alignment on other pre-identified portions of the reference dataset that are known to be related to that pre-identified portion. For instance, the four identifiers of the read 1002 may be compared against each of the five different contiguous groups of four identifiers in the first part 1006 to generate five alignment scores. Of these scores, it may be that the score associated with the first group of four consecutive identifiers in the first part 1006 is the greatest or meets a threshold. It may be determined that this score and the associated identifiers are for the first pre-identified portion 1016. In a database, there may be a pre-determination that the first pre-identified portion 1016 is related to other portions of the reference dataset 1004, such as the second pre-identified portion 1018. Thus, since the alignment result includes the first pre-identified portion 1016, the assessment system may automatically determine that an alignment also needs to be performed on the second pre-identified portion 1018 due to the relation. Or the assessment system may simply permit the read to be aligned to the second pre-identified portion 1018. In various instances, there may be multiple pre-identified portions of the reference dataset that are related to a pre-identified portion that has met the initial alignment condition (e.g., has a score above a threshold), or there may be no related pre-identified portions.

Thus, in this example, a score associated with a first alignment (with the left-most identifier of reach 1002 aligning with the left-most identifier of the first part 1006 of the reference dataset) may be higher than the other four scores associated with the first part 1006. Based on a score comparison and/or threshold analysis, the first alignment can be identified as an alignment or potential alignment for the read. In some instances, a task is performed (e.g., after aligning each individual task or after aligning all tasks) to determine which reads (if any) overlap (e.g., to a defined degree) with any of one or more pre-identified portions. Each pre-identified portions may correspond to a corresponding pre-identified portion. For example, with respect to a pair of pre-identified portions, one portion may represent a pseudogene and another portion may represent a corresponding gene (or part thereof). One or more queries may be performed to identify reads that overlap (e.g., to a defined degree) with any of one or more pre-identified portions. For example, for each read, a database may be queried with a start and stop position of an alignment result, and a result may identify whether the positions overlap with a pre-identified portion (e.g., by identifying any positions between the start and stop position corresponding to a pre-identified portion and/or identifying the pre-identified portion). As another example, read-alignment data may be queried to identify, for each of one or more pre-identified portions, which reads overlap with the portion and to what extent.

In the illustration of FIG. 10, different machines are assigned to process potential alignments with respect to parts of the reference dataset that correspond to corresponding pre-identified portions. Thus, each machine may independently identify a potential alignment with one of the two corresponding pre-identified portions. Thus, Machine 1 may identify the read as aligning to (or potentially aligning to) first pre-identified portion 1016, and Machine 2 may identify the read as aligning to (or potentially aligning to) second pre-identified portion 1018, due to (for example) scores associated with the portion being higher than scores of any other considered alignment and/or a predefined absolute threshold. It will be appreciated that a similar result may be obtained if a single machine perform alignments with the read 1002 using the entire reference dataset 1004, as the machine may detect scores associated with each pre-identified portions as exceeding a predefined threshold. Upon detecting multiple potential alignments (via one or more machines), it may be determined whether each of the multiple potential alignments overlap (e.g., by at least a threshold degree) with one of multiple corresponding pre-identified portions. Multiple alignments may be permitted when the alignments are to corresponding pre-identified portions but, in some instances, not otherwise (e.g., such that a single alignment is to be selected based on, for example, scores of each alignment).

In some embodiments, the reference dataset 1004 may be divided up among the machines such that each part of the reference dataset 1004 received by a machine does not start or terminate at a position in the middle of a known pre-identified portion.

Thus, in some embodiments, the machines may determine any portions of the reference dataset 1004 associated with any alignment scores above a given threshold. As previously described, there may be one or more alignment scores that are above a relative or absolute threshold. The machines may then determine that alignment scores above the threshold are associated with pre-identified portions (e.g., the first pre-identified portion 1016 or the second pre-identified portion 1018). For instance, the first pre-identified portion 1016 is determined as being associated with an alignment score above the threshold. Upon determining that an alignment score above the threshold is associated with the first pre-identified portion 1016, the first pre-identified portion 1016 can be identified in an alignment result along with any other pre-identified portions (e.g., the second pre-identified portion 1018) that are known to be related to that pre-identified portion.

In some instances, it can be determined whether a preliminary alignment result (e.g., being associated with a top score or a score above a predefined threshold) corresponds to an alignment exception. An alignment exception can be defined to apply when (for example, and in various embodiments), a read is aligned to a portion that is at all overlapping, overlapping by at least a threshold amount (e.g., number of identifiers or percentage of the read), or entirely aligned within any of one or more pre-identified portions. Thus, in the example shown in FIG. 10, the alignment exception may be determined to apply, given a result from one or both of the first machine 1010 or the second machine 1012.

In some embodiments, the alignment results from the first machine 1010 and the second machine 1012 may be merged to produce a combined alignment result 1014. The combined alignment result 1014 may provide an indication of each portion in the reference dataset 1004 that is identified as an alignment (e.g., associated with an alignment score above the threshold or known to be related to a portion having an alignment score above the threshold). For example, in the example shown of the combined alignment result 1014 it can be seen that there are two different portions of the reference dataset 1004 associated with alignment scores above the threshold (the first pre-identified portion 1016 and the second pre-identified portion 1018).

Figure 11:
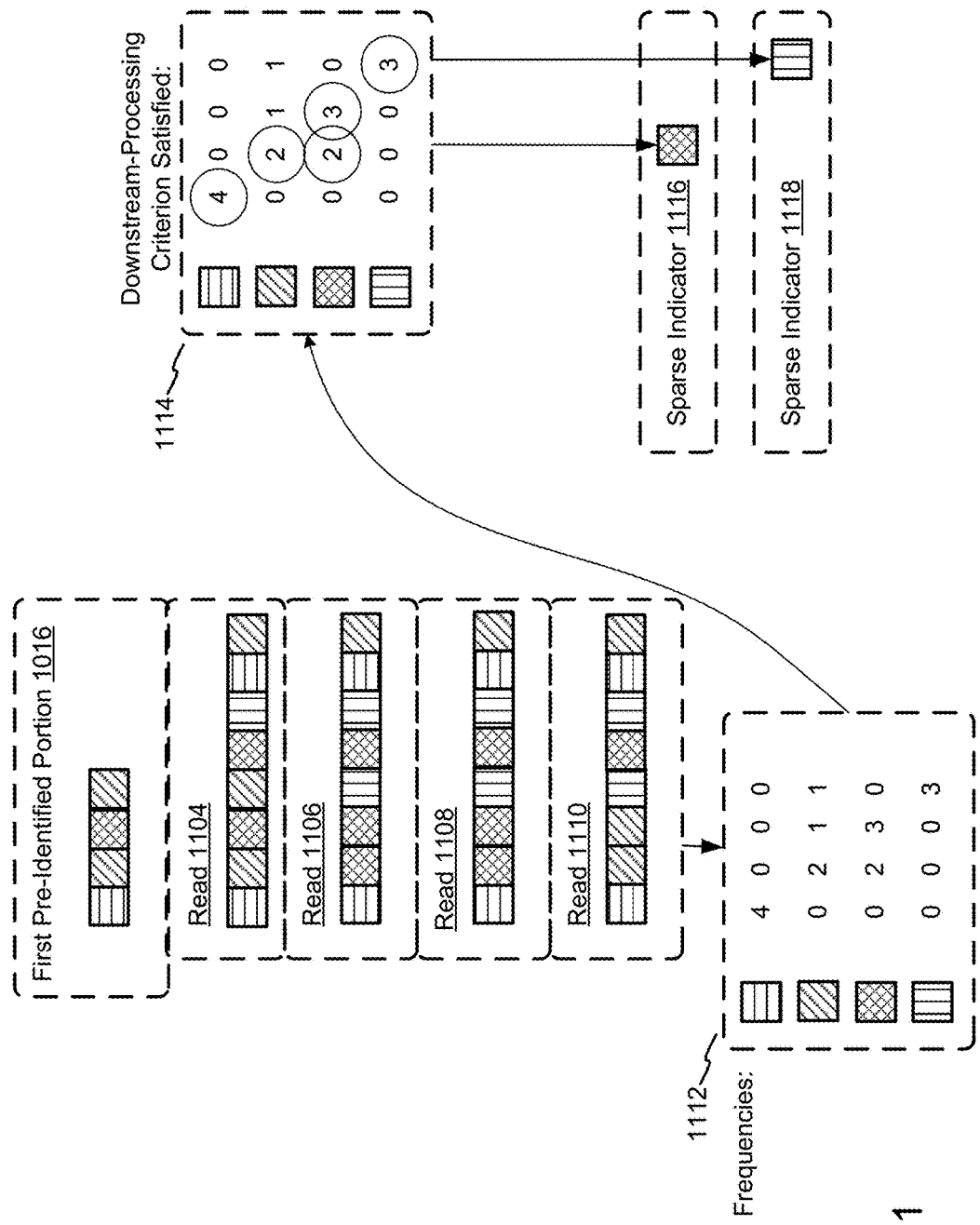
FIG. 11 illustrates a process for determining sparse indicators in accordance with embodiments of the present disclosure.

FIG. 11 illustrates a process for determining sparse indicators in accordance with embodiments of the present disclosure. The depicted representation corresponds to a processing involving the first pre-identified portion 1016 of the previous figure, which was associated with an alignment score above the threshold.

A number of reads provided to a machine (e.g., a subset of the set of reads provided to the machine) may align to the first pre-identified portion 1016. For example, the subset of reads may include read 1104, read 1106, read 1108, and read 1110. As shown in the figure, the first identifier in each of those reads is aligned to the identifier in the first position of the first pre-identified portion 1016. However, in practice, any identifier in the reads may be aligned to the identifier of the first position of the first pre-identified portion 1016. Furthermore, the reads may be of various lengths. Although not shown, this process may also be performed for any pre-identified portions of the reference dataset that are known to be related to the first pre-identified portion 1016.

The quantity, or frequency, of identifiers among the subset of reads at each position of the first pre-identified portion 1016 can be determined. For instance, the frequencies among reads 1104, 1106, 1108, and 1110 are represented in example frequency table 1112. The first type of identifier occurs four times among the reads at the first position of the first pre-identified portion 1016. At the second position, there are two occurrences of the second type of identifier and two occurrences of the third type of identifier. At the third position, there is one occurrence of the second type of identifier and three occurrences of the third type of identifier. At the fourth position, there is one occurrence of the second type of identifier and three occurrences of the fourth type of identifier.

In some embodiments, the quantity of a type of identifier among the subset of reads at a position of the first pre-identified portion 1016 may be used to determine whether an downstream-processing criterion is satisfied at that position. The downstream-processing criterion may be configured such that satisfaction of the criterion triggers performance of one or more particular tasks (e.g., identify one or more client-data values for each of one or more positions, performing a sparse-indicator detection, classifying any sparse indicators, etc.).

In the depicted instance, a downstream-processing criterion table 1114 is shown. With regard to this example, the downstream-processing criterion may be satisfied at least a particular percentage (e.g., 50%, 75%, 100%, etc.) of reads include a certain type of identifier at that position. For instance, the downstream-processing criterion in the figure may be 50%. At the first position, 100% of the identifiers among the subset of reads are of the first type which means the first type of identifier satisfies the downstream-processing criterion for the first position. At the second position, both the second type and third type of identifiers occur 50% of the time which means both of those types of identifiers meet the downstream-processing criterion for the second position. At the third position, the third type of identifier occurs 75% of the time which means the third type of identifier satisfies the downstream-processing criterion for the third position. At the fourth position, the fourth type of identifier occurs 75% of the time which means the fourth type of identifier satisfies the downstream-processing criterion for the third position. In some embodiments, a representation metric may be defined for the various positions which is the quantity of a type of identifier at a position among the reads in the subset divided by the number of reads in the subset, wherein the downstream-processing criterion is configured to be satisfied when the representation metric exceeds a threshold. For example, a representation metric of 50% would be satisfied if half or more of the identifiers at a certain position among the reads in the subset were of a specific type of identifier.

The types of identifiers that meet the downstream-processing criterion at each position can be compared to the identifiers of the reference dataset (e.g., the first pre-identified portion 1016) in order to determine whether a sparse indicator is detected, the sparse indicator potentially representing a difference between the client-data identifier and a reference-data identifier. For example, in the depicted illustration, at the first position, the downstream-processing criterion is satisfied by the first type of identifier. The identifier at the first position of the first pre-identified portion 1016 is also of the first type, which is a match. At the second position, the downstream-processing criterion is satisfied by both the second type and third type of identifier. However, the identifier at the second position of the first pre-identified portion 1016 is the second type. The third type of identifier, identified to meet the downstream-processing criterion at the second position, is different from this second type of identifier which means the third type of identifier is a sparse indicator 1116 at the second position. Similarly, at the fourth position, the downstream-processing criterion is satisfied by the fourth type of identifier. However, the identifier at the fourth position of the fourth pre-identified portion 1016 is the second type of identifier. This means that the fourth type of identifier is a sparse indicator 1118 at the fourth position. After the sparse indicator 1116 and the sparse indicator 1118 are identified, they can be assigned to a bucket representative of a state-transition likelihood attributable to the sparse indicator.

Figure 12:
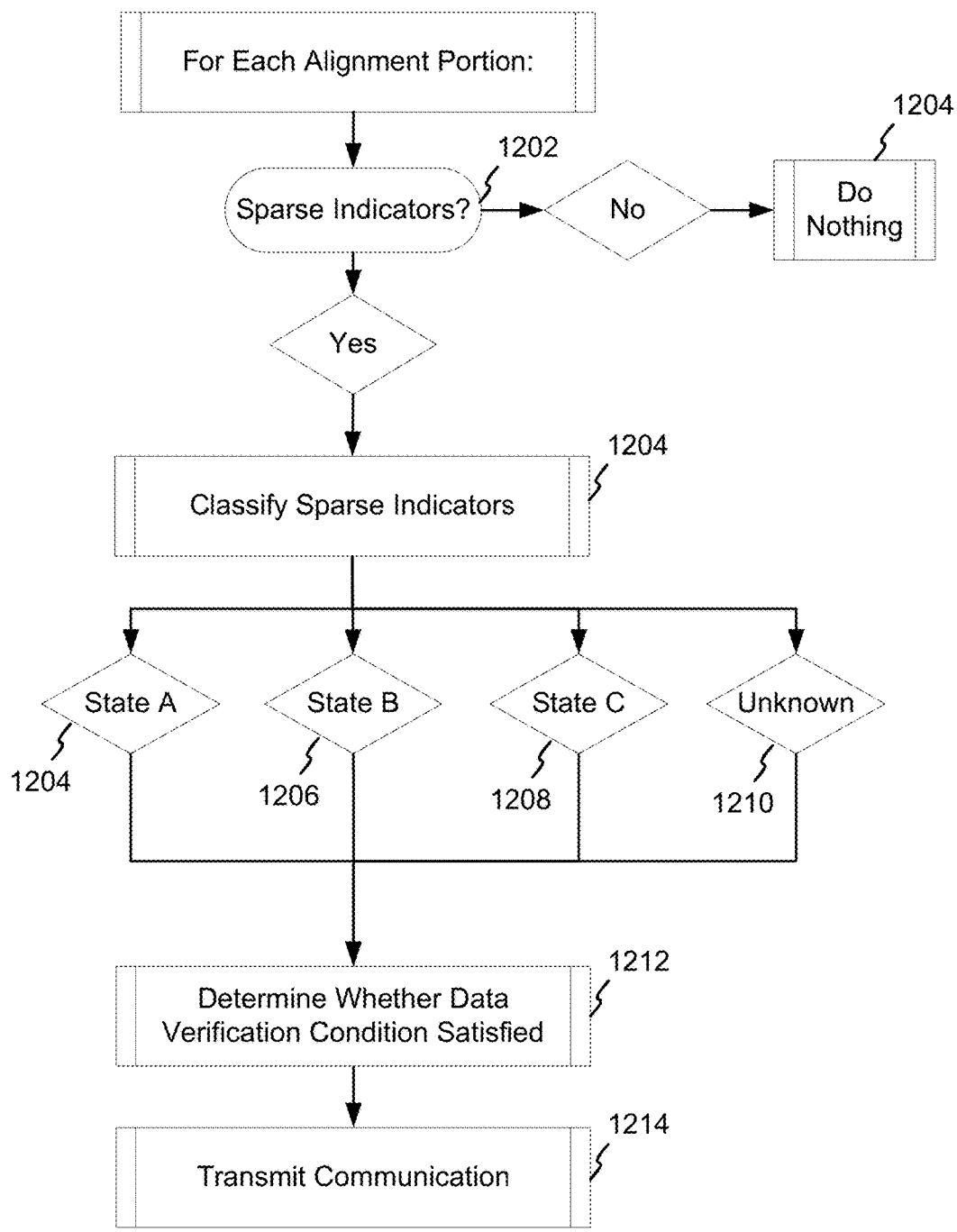
FIG. 12 illustrates a flowchart for detecting potential sparse indicators in pre-identified alignment portions in accordance with embodiments of the present disclosure.

FIG. 12 illustrates a flowchart for detecting potential sparse indicators in pre-identified alignment portions in accordance with embodiments of the present disclosure. At block 1202, for each pre-identified alignment portion of the reference dataset (e.g., the first pre-identified portion 1016 or the second pre-identified portion 1018) a determination can be made over whether that alignment portion has one or more sparse indicators. If the alignment portion has no sparse indicators at all (e.g., for each position evaluated in association with the portion, one or more identifiers generated based on the aligned reads are identical to an identifier at the position in alignment portion), then at block 1204 no action is performed and the next alignment portion can be considered. If none of the alignment portions have any sparse indicators, it may be concluded that a state-transition likelihood does not depend to which pre-identified portion (or part thereof) a client's reads are aligned.

If an alignment portion is associated with one or more sparse indicators (or potential sparse indicators), then at block 1204 each of the sparse indicators (or potential sparse indicators) of that alignment can be classified. The sparse indicator(s) (or potential sparse indicator(s)) for each alignment portion can be classified based on a state transition likelihood associated with that sparse indicator. Some examples of classifications that the sparse indicators can be classified under include state A 1204, state B 1206, state C 1208, unknown 1210, and so forth. For example, if every sparse indicator (or potential sparse indicator) for that alignment portion is classified as state A, then that alignment portion may not, in some instances, influence a determination of a state transition likelihood. Furthermore, if every sparse indicator for every alignment portion is classified as under state A, then (in some instances) it may be concluded that a state-transition likelihood does not depend to which pre-identified portion (or part thereof) a client's reads are aligned. In some embodiments, if a sparse indicator is classified as state A it may (but need not) be reported to a client with a flag reflecting decreased confidence.

At block 1212, a determination can be made regarding whether a data verification condition is satisfied. In some embodiments, the data verification condition may be satisfied if any of the sparse indicators are determined to be of a certain state, such as state B 1206, state C 1208, or unknown 1210 (e.g., pathogenic, likely pathogenic, or unknown). In some embodiments, the data verification condition may be satisfied if the determination of a state transition likelihood or state transition metric exceeds a certain threshold. If the data verification condition is satisfied then at block 1214, a communication may be sent to the data generator system (or the client 125 or facility 120) in order to confirm data (e.g., one or more reads) and/or to request new data (e.g., corresponding to a new processing of a sample using a different processing type to produce longer reads to aid alignment).

Figure 13:
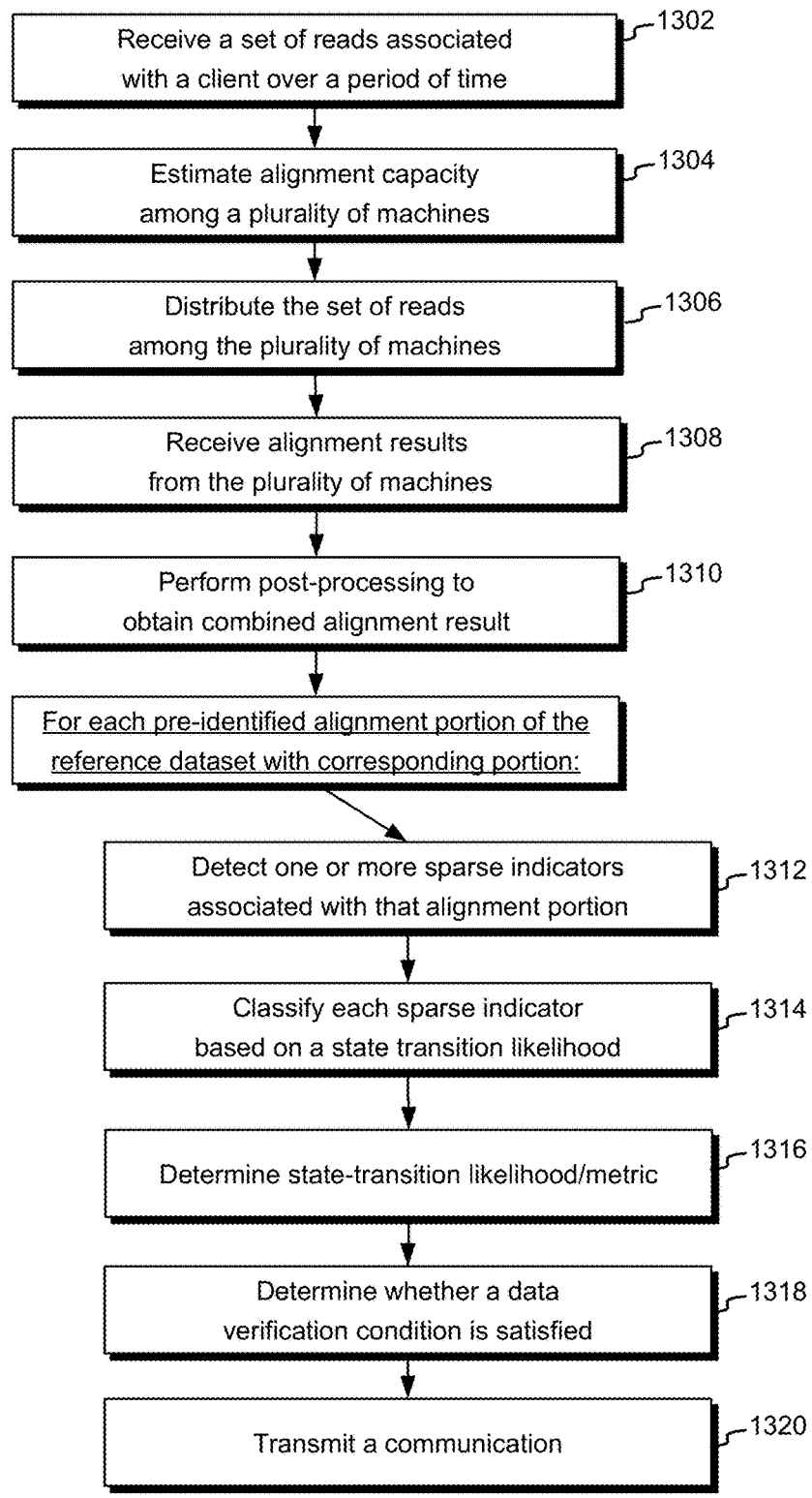
FIG. 13 illustrates a flowchart for distributing alignment tasks across a plurality of machines in accordance with embodiments of the present disclosure.

FIG. 13 illustrates a flowchart for distributing alignment tasks across a plurality of machines in accordance with embodiments of the present disclosure. This figure provides an overview and summary of FIGS. 9-12.

At block 1302, the assessment system may receive a set of reads associated with a client over a period of time. In some embodiments, the set of reads associated with the client may be data generated by one or more devices associated with the data generator 140 based on material associated with a client, such as a sample of material provided by the client 125. Accessing the set of reads may include receiving the set of reads (e.g., from data generator 140) or retrieving the set of reads from a local or remote storage. In various instances, the set of reads may be transmitted to the assessment system in a batch-mode, in a streaming mode, in real-time as data is produced, and/or upon request. Thus, not all of the reads associated with the client may be received at one point in time. However, each of these reads may be associated with data for identifying the client (e.g., client-identifying data), such as a client id. Thus, even though the reads for the client may be received in separate batches, the set of reads for the client can be determined based on the client-identifying data (e.g., sorting based on client id).

At block 1304, the assessment system may estimate the alignment capacity among a plurality of machines. In some embodiments, this can be performed by the scheduler 912 shown in FIG. 9. The assessment system may be configured to distribute alignment tasks among the plurality of machines while balancing the resource utilization across the plurality of machines. This may involve determining the available alignment capacity at each individual machine.

At block 1306, the alignment capacity among the plurality of machines can be used in order to distribute alignment tasks for the set of reads for the client among the plurality of machines. The data for the set of reads may also need to be distributed among the plurality of machines. As previously mentioned, the distribution of alignment tasks across the plurality of machines can be done (for example) in two dimensions. For example, each of the machines could be configured to align a read against the entire reference dataset. In this case, the set of reads for the client can be broken up and distributed to the machines, such that one machine will get some of the reads for the client, another machine will get other reads for the client, and so forth. Alternatively, each of the machines could be configured to align a read against just a part of the reference dataset. In this case, each read in the set of reads for the client would have to be provided to each machine (e.g., every machine receives the whole set of reads). This would require the optional post-processing step to be performed at block 1310 in order to merge the alignment results produced by each of the machines for a particular read.

At block 1308, the alignment results can be received from the plurality of machines. If one of the machines was tasked with aligning a particular read against the entire reference dataset, then the alignment result provided by that machine will already identify all the alignment portions of the reference dataset for that read (and optional block 1310 will not need to be performed). However, if multiple machines were tasked with performing alignments using different parts of the reference dataset, then post-processing may be performed.

At optional block 1310, alignment results generated by different machines can be merged in order to obtain a combined alignment result that indicates all the alignment portions of the entire reference dataset for that read. In some instances, each identified alignment portion is included in the combined result. In some instances, a particular number (e.g., one) of alignment portions identified by different machines is identified to be solely included in the combined result (e.g., the number corresponding to the portion(s) with the highest score(s)). In some embodiments, this step may involve checking a database to identify any known pre-identified portion of the reference dataset that are related to a portion of the reference dataset identified by a machine in an alignment result. For example, the step may typically involve selecting a top-score alignment result from amongst the results produced by machines unless it is determined that a top-score alignment result corresponds to a pre-identified portion (e.g., in which case another alignment result associated with a corresponding pre-identified portion may be permitted to also be included (e.g., if a score is above a threshold) and/or automatically included).

The alignments may then be used to generate a client data set, detect any sparse indicators, classify any sparse indicators and/or generate a state-transition likelihood, as disclosed herein. It will be appreciated that each of one or more of these tasks may be distributed across a same or different plurality of machines.

Further, as disclosed herein, a separate and/or preliminary analysis may be conducted (using one or more machines) with respect to each pre-identified alignment portion (e.g., having a corresponding portion). In FIG. 12, blocks 312-1320 are performed for each pre-identified alignment portion.

At block 1312, for each pre-identified alignment portion, a sparse-indicator detection is performed to detect any sparse indicators associated with the portion. The sparse-indicator detection may be the same as one performed for other portions in the reference data set (e.g., without corresponding portions). For example, the sparse-indicator detection at block 1312 may use a lower threshold with respect to identifying a percentage of reads that must have a same value before comparing the value to a corresponding reference-data value for sparse-indicator detection. As another example, the sparse-indicator detection at block 1312 may permit comparing multiple client-data identifiers to be detected with respect to reference-data identifiers at a single position and each identified as a sparse indicator or potential sparse indicator (e.g., whereas sparse-indictor detection may normally only allow comparing a single client-data identifier to a reference-data identifier).

At block 1314, each sparse indicator can be classified and assigned to various buckets (e.g., including one of multiple buckets, such as amongst bucket types described herein). Assignments to one or more particular buckets may be such to not increase (or potentially increase) a state-transition result, while assignments to one or more other particular buckets may increase (or potentially increase) a state-transition likelihood.

At block 1316 the determination of a state transition likelihood or state transition metric may be determined. The determination may include determining a state-transition metric or likelihood based on the sparse-indicator detection and/or sparse-indicator classification. For example, if no sparse indicators ere detected or if each detected sparse indicator was classified to a bucket that does not correspond to an increase (or potential increase) in a state-transition likelihood, then the state-transition likelihood or metric may be determined based on any sparse indicators detected in one or more other (e.g., not pre-identified) portion and/or other data.

At block 1318, a determination can be made regarding whether a data verification condition is satisfied. In some embodiments, the data verification condition may be configured to be satisfied when (for example) a quantity of sparse indicators assigned to any of one or more particular buckets exceeds a threshold. In some cases, this threshold might be zero. For instance, if at least one sparse indicator is assigned to either a pathogenic or likely pathogenic classification (or unknown), then the data verification condition would be satisfied. If an alignment portion has no sparse indicators, then, in some instances, the data verification condition would not be satisfied for that alignment portion. Thus, in some embodiments, the data verification condition may be satisfied if the determination of the state transition likelihood or state transition metric exceeds a certain threshold. If the data verification condition is satisfied then at block 1320, a communication may generated and transmitted the data generator system (or the client 125 or facility 120) in order to re-generate or confirm the read, or to confirm the presence of pathogenic or likely pathogenic sparse indicators. The communication may identify the client, the read, and/or the alignment portion(s) of the reference dataset with the sparse indicators that triggered the data verification condition.

Figure 14:
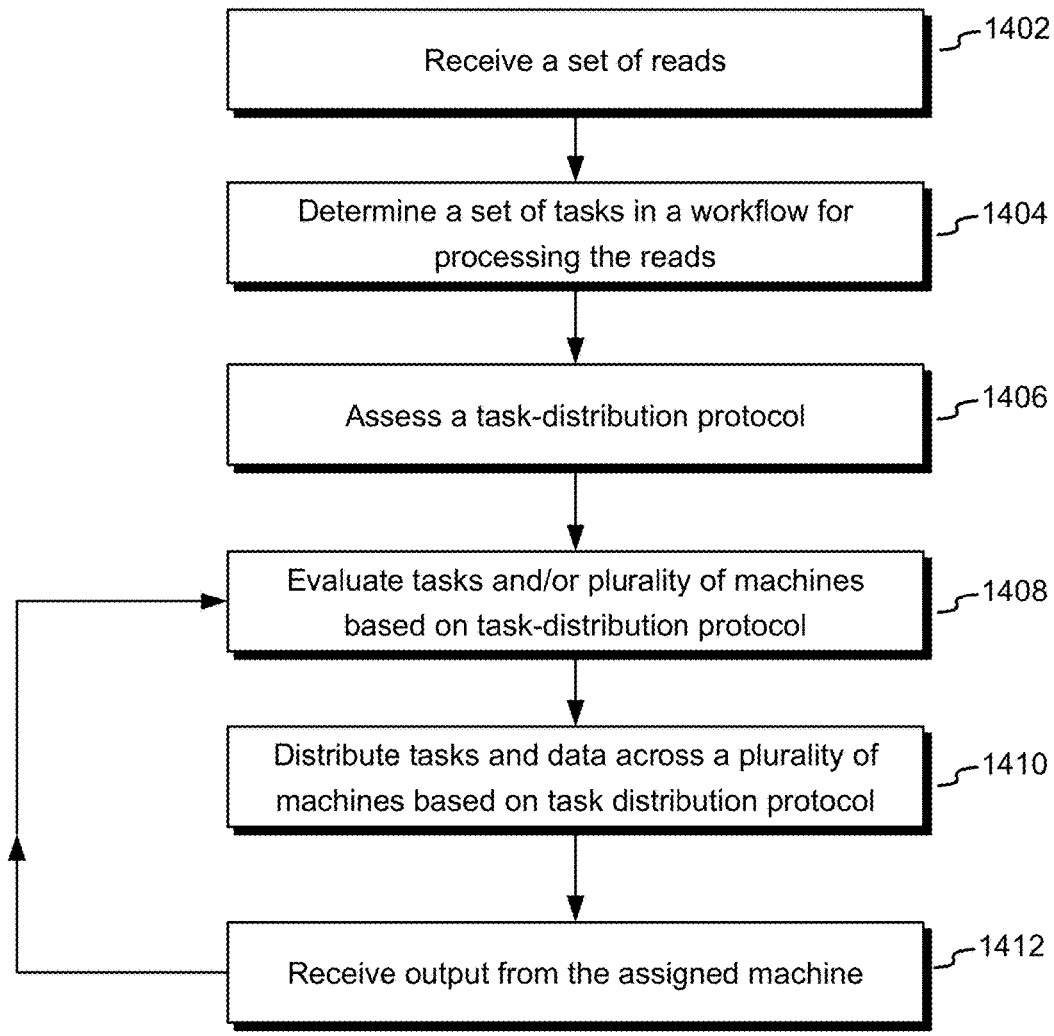
FIG. 14 illustrates a flowchart for the distribution of tasks associated with processing reads across a plurality of machines in accordance with embodiments of the present disclosure.

FIG. 14 illustrates a flowchart for the distribution of tasks associated with processing reads across a plurality of machines in accordance with embodiments of the present disclosure.

At block 1402, the assessment system may receive a set of reads (e.g. from one or more laboratories or data generator systems) over a period of time. The set of reads may be associated with a single client or sample, or multiple clients or samples. In order to facilitate understanding, the processing of the set of reads is described in the context of the set of reads being associated with a single client.

At block 1404, the assessment system may determine a set of tasks in a workflow for processing the reads. In some embodiments, this set of tasks may be defined by a protocol. In some of such embodiments, this protocol may be a task-distribution protocol. These tasks may involve processing steps for processing reads to determine a state-transition likelihood, and may include alignment tasks, sparse indicator detection, sparse indicator classification, determination of state-transition likelihood, determination of whether a data verification condition is satisfied, and generating and/or sending a communication.

At block 1406, the assessment system may assess a task-distribution protocol, which may define how the different tasks are to be distributed among the various machines for processing.

At block 1408, the assessment system may evaluate the tasks and/or the machines based on the task-distribution protocol, and at block 1410, the assessment system may distribute the tasks and the data for those tasks among the machines based on the task-distribution protocol. The assigning each task of the plurality of the tasks or the defining the plurality of tasks can be performed in accordance with a task-distribution protocol that uses a processing characteristic of each task. For example, if the task is an alignment task, the processing characteristic for that task may include how many potential alignments were identified as corresponding to the read, a length of the read, and/or a degree to which the read matched portions of a reference dataset. Thus, in this example, reads associated with multiple alignments of the reference dataset, or reads of longer length, may be predicted to require more computational resources for different tasks involving those reads (e.g., the detection of sparse indicators for a longer read that would take more resources as well). Accordingly, tasks involving such reads may be assigned to a machine with greater processing capabilities and/or can be assigned with fewer other tasks to a given machine. At least one first task of the plurality of the tasks can be assigned to a machine different than a machine to which at least one second task of the plurality of tasks is assigned.

At block 1412, the assessment system may receive outputs from the machines that have been assigned tasks. For example, if an alignment task for a read was distributed to a machine, an alignment result for the read may be received from the machine. The alignment result may indicate how many portions of a reference dataset the read aligns, to which portion(s) of a reference dataset the read aligns, a confidence of an alignment and/or match score, and so forth. The alignment result may be transmitted with an identifier.

Over a period of time, the assessment system may continue evaluating any remaining tasks and the capabilities of the machines (e.g., block 1408), distributing those tasks to the machines based on the task-distribution protocol (e.g., block 1410), and receiving outputs for tasks assigned to the machines (e.g., block 1412) until there are no more tasks to distribute to the machines.

In some embodiments, at block 1408 the assessment system may take into consideration a processing characteristic associated with each task. This processing characteristic may be generated for each task to be distributed, and the processing characteristic may reflect a resource usage for that task. In one instance, the processing characteristic corresponds to a time-series function, where the processing characteristic represents a predicted processing required at each of multiple time points within the time series. It will be appreciated that the processing characteristic may additionally or alternatively correspond to use of another resource component, such as memory. The processing characteristic may be generated based on one or more characteristics of the read (e.g., a length), a result of prior read processing, and/or preliminary or previous analyses (e.g., a determination as to how many portions of a reference dataset that the read aligns with at an above-threshold alignment or match score). Thus, at block 1410, the tasks may be distributed based on the processing characteristics associated with each task. In some cases, each of the tasks may correspond to a similar predicted resource usage. In various instances, a single task may involve multiple reads and/or a single read.

At block 1410, the tasks may continue to be distributed among a plurality of machines as the machines become available over a period of time (e.g., each time point from a plurality of time points). The plurality of time points can include, for example, time points defined based on events. For example, each time point may correspond to a time at which an indication is received from a machine that the machine is, or is to be, available for processing. The indication can be associated with, for example, a communication corresponding to a request for a processing task and/or a communication corresponding to an indication that a previous task has been completed. A task can then be distributed to that machine based on the task-distribution protocol. The selection may be made, for example, by selecting a task using a pseudo-random selection technique, selecting a task using a consecutive selection, and/or selecting a task having a processing characteristic that corresponds to the processing characteristic of another task that has been processed by the machine. For example, if a given machine performed alignment tasks for a set of reads, a selection may subsequently be biased towards tasks that correspond to other processing steps for one or more reads of that set of reads. The corresponding data needed to perform the selected task may also be sent to the machine (e.g., data for the read).

In some embodiments, a task may involve processing of multiple reads, and the reads may be grouped in a manner to produce different tasks of similar predicted resource usage. Tasks can then be assigned to machines semi-evenly. This may be particularly advantageous when distributing task processing to multiple machines with similar process capacities. However, in other embodiments, the task blocks may be defined differently (e.g, a first set of task blocks may be configured to each have a first predicted resource usage and a second set of task blocks may be configured to each have a second predicted resource usage) if the machines are associated with different resource capacities.

It should be further noted that the specific implementation details associated with each of block 1408, block 1410, and block 1412 may depend on the specific type of task being distributed to the machines. As previously mentioned, some examples of the types of tasks involved in the processing of a read include alignment tasks, sparse indicator detection, sparse indicator classification, determination of state-transition likelihood, determination of whether a data verification condition is satisfied, and generating and/or sending a communication.

For example, in some instances, the assessment system may be distributing alignment tasks among the machines. Thus, at block 1408, an alignment capacity of each machine can be estimated. The alignment capacity can include a general capacity, current capacity and/or predicted capacity. The alignment capacity may be estimated based on, for example, one or more specifications of the machine (e.g., storage, processor, etc.). The alignment capacity may depend on tasks previously assigned to the machine. A machine may be identified from amongst the plurality of machines to perform an alignment technique on a read. The identification may be performed using a task-distribution protocol and at least one estimated alignment capacity. For example, machines with larger alignment capacity may be assigned more (e.g., quantity) or more complicated (e.g., longer) reads to align than other machines. The task-distribution protocol may be configured so as to attempt to divide alignment tasks, or tasks in general, evenly across machines. Such division may be focused on numbers of tasks, task time and/or task processing. At block 1410, the read may be transmitted to the identified machine along with an identifier. The identifier may include an identifier of the read, corresponding client or corresponding sample. The transmission may include transmission of a communication that includes this data and/or identification that this data is to be retrieved from a storage component or storage device. At block 1412, the assessment system would receive an alignment result for that read from the machine. The alignment result may indicate how many portions of a reference dataset the read aligns, to which portion(s) of a reference dataset the read aligns, a confidence of an alignment and/or match score, and so forth. This alignment result may also be transmitted with an identifier.

As another example, in some instances, the assessment system may be distributing tasks for the detection of sparse indicators within one or more reads. Each of these tasks may include detecting whether and which sparse indicators are included within one or more reads of the set of reads. Thus, at block 1410, each sparse indicator determination task may be assigned to a machine of a plurality of machines. The corresponding data for the task may be sent as well (e.g., a read, the corresponding alignment results for the read, the reference dataset, and so forth). This assignment can be performed in accordance with the task-distribution protocol, which may use a characteristic of each read of the set of reads and the alignment results. For example, the characteristic can include how many potential alignments in the reference dataset were identified as corresponding to the read, a length of the read, and/or a degree to which the read matched a corresponding portion of the reference dataset. Thus, for example, reads associated with multiple potential alignments in the reference dataset, or reads that are of longer length, may be predicted to require more computational resources for the determination of sparse indicators.

In some embodiments, a client data set may be generated from the set of reads associated with a client, and the client data set may include a plurality of data elements. Each data element of the plurality of data elements can correspond to a single client or sample. Each data element of the plurality of data elements can be defined based on an alignment performed by a machine of the plurality of machines. At least one data element of the plurality of data elements can be based on an alignment performed by a machine different than a machine that performed an alignment upon which at least another data element of the plurality of data elements is based. One, more or each data element in the plurality of data elements may include, for example, an alignment result. One, more or each data element in the plurality of data elements may include, for example, a sparse indicator detection (e.g., whether and/or which sparse indicators were detected in a read, which may have been detected using the alignment). In some instances, each read is represented in the data set. In some instances, each read for which an alignment result indicates that the read aligns with a portion of a reference dataset that is of interest for an analysis is included (e.g., and not reads for which an alignment result indicates that the read is not aligned with a portion of reference dataset that is of interest for an analysis).

In some embodiments, a determination of a state-transition likelihood may be generated based on sparse indicators identified from the reads of a client. In some cases, this data may come from the client data set. For example, the client data set may be used to identify reads corresponding to portions of a reference dataset, and those reads may be analyzed for differences from the reference dataset to determine sparse indicators that may be further classified and assessed in order to determine the state-transition likelihood.

Figure 15:
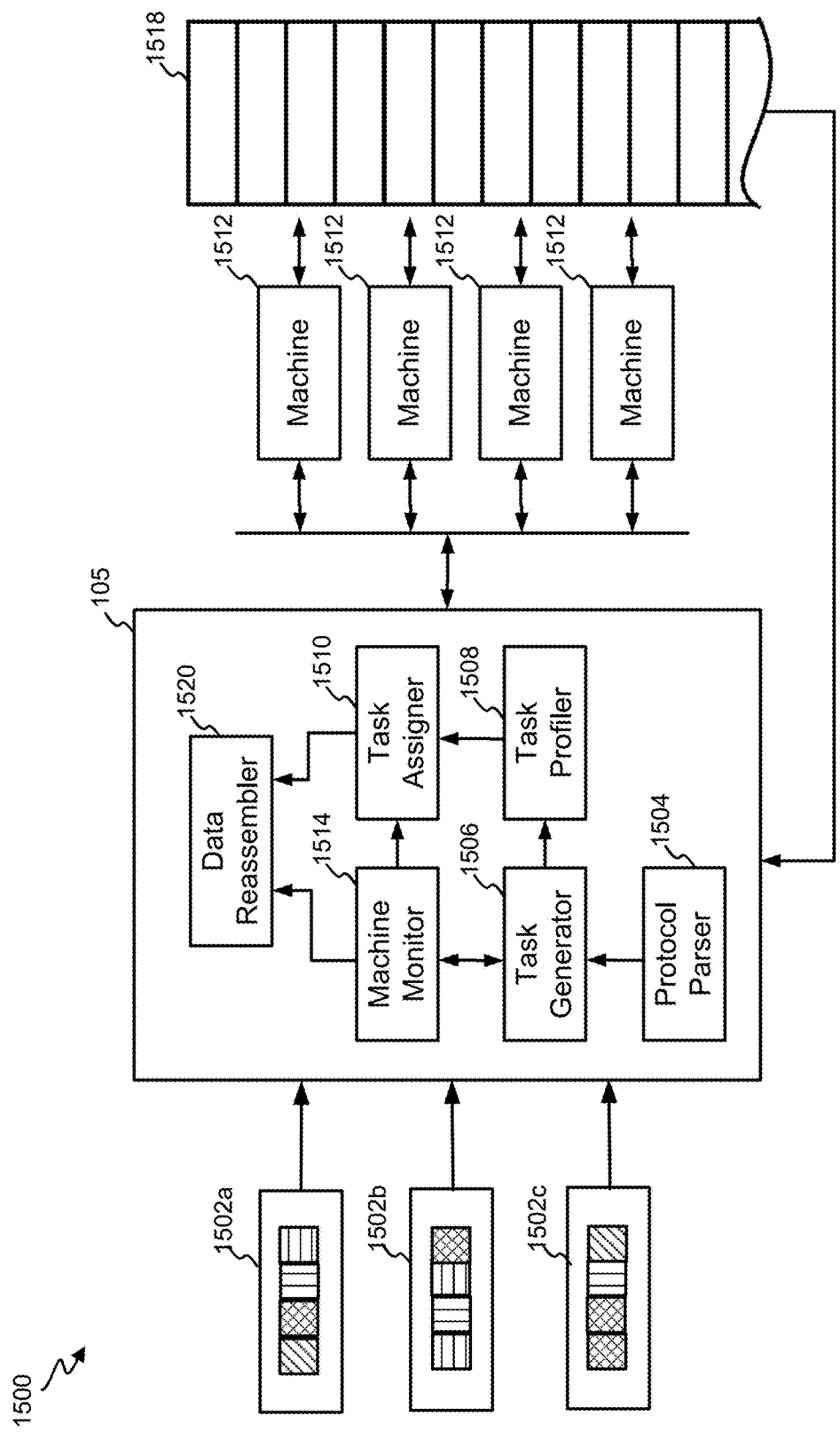
FIG. 15 illustrates a flowchart for distributing alignment tasks (e.g., for load-balancing and task distribution) across a plurality of machines in accordance with embodiments of the present disclosure.

FIG. 15 illustrates a flowchart for distributing alignment tasks (e.g., for load-balancing and task distribution) across a plurality of machines in accordance with embodiments of the present disclosure. This figure may be related to the implementations of load-balancing and task distribution shown in FIGS. 9, 13, and 14.

In the flowchart of FIG. 15, the distributed processing 1500 of data is shown. For instance, there may be multiple reads 1502*a*, 1502*b*, and 1502*c* that are received by the assessment system 105 (in practice, there may be many more reads). In this illustrated example, the reads 1502*a*, 1502*b*, and 1502*c* may all correspond to a single client and sample, or they may correspond to different clients or samples. The reads 1502*a*, 1502*b*, and 1502*c* may be received from, for example, a laboratory system.

In some embodiments, the assessment system 105 may include a protocol parser 1504. A protocol may identify multiple steps or tasks in a workflow to be taken in order to transform read data into a determination of a state-transition likelihood. The steps may include, for example, performing an initial alignment of each read in a set of reads against a reference dataset, performing subsequent processing on reads with particular types of initial alignment results, detecting sparse indicators associated with the reads, classifying the sparse indicators, and using the sparse indicator classifications to determine a state-transition likelihood. Some steps may require processing of individual reads. Some steps may require processing of aggregated data. In some embodiments, the protocol may additionally be a task-distribution protocol, which may define a set of rules or criteria for distributing the tasks of the protocol among a plurality of machines configured to perform those tasks.

The protocol parser 1504 may be able to identify distinct processing actions to be performed for one or more analyses to be performed with respect to incoming reads. For each action, data required for processing can be identified. The protocol parser 1504 may identify action dependencies, such as indications when select actions require completion of one or more other select actions before the select action can be performed. In some instances, the protocol parser 1504 can identify which different actions can be performed in parallel (e.g., for a given client analysis) and/or whether, for a particular action, different reads can be performed in parallel.

In some embodiments, a task generator 1506 may define individual tasks to be performed by individual machines. Each task can correspond to, for example, one of the parsed actions. Further, defining a task can include identifying what data is to be processed. The data may include; for example, one or more reads, a reference dataset (or one or more portions of a reference dataset and/or one or more results from previous processing for a client.

In some embodiments, a task profiler 1508 may identify a processing characteristic associated with each generated task. The processing characteristic can represent predicted resource usage for completing that task. The processing characteristic of a task can be determined, for example, based on a size of data to be processed, resource usages previously detected for similar types of processing, and/or previous results corresponding to the data (e.g., identifying an initial alignment result). The processing characteristics associated with the tasks of a workflow defined by the protocol are further described in FIG. 16.

In some embodiments, a task assigner 1510 may assign each task to one of a plurality of machines 1512. The assignment of a task can be based on the rules of the task-distribution protocol, the profile associated with the task (e.g., task profile), the action to be performed in the task (e.g., task action), the capabilities of the various machines 1512, the current availabilities (e.g., usage or load) of the various machines 1512, and/or the queues or data access of the various machines 1512. Thus, the task assigner 1510 may communicate with a machine monitor 1514, which may monitor (for example) a current or prospective load at each of one or more machines, a task-completion time at each of one or more machines, and/or a specification of each of one or more machines. The machine monitor 1514 may also alert task generator 1506 if the machine monitor 1514 detects an instance where it appears as though completion of an assigned task may be delayed or unlikely. Such an alert may be pushed from the machine monitor 1514 or communicated in response to a status request from task generator 1506. The task generator 1506 may then generate a new task such that a different machine can handle the new task.

Upon assigning a task, the assessment system 105 can communicate the corresponding data to the machine 1512 to which the task was assigned. The data may include, for example, a read (or identification thereof), a task identifier, a reference dataset or portion of a reference dataset (or identification thereof), a task variable, a result of a prior processing corresponding to a read, an identifier of a client, and/or an identifier of a sample.

After the machine 1512 receives the task assignment and the corresponding data needed to perform the task, the machine 1512 may then perform the task and produce a result 1518 that may be stored in a data store (e.g., a cache data store, RAM data store, or other memory), added to a result stream and/or communicated (e.g., back to the assessment system 105).

In some embodiments, there may be a data reassembler 1520 that aggregates a collection of results (e.g., including result 1518). The collection of results can correspond to, for example, some or all results corresponding to a given client or sample. For example, the results aggregated may include one or more sparse indicators detected for reads aligned to particular portions of a reference dataset. The reassembled data may then be used as data to be processed in accordance with one or more other actions. Thus, the task generator 306 may generate another task to process the aggregated data.

Thus, the depicted data flow may involve a degree of data feedback in the implementation of using parallel processing to perform data analysis.

Figure 16:
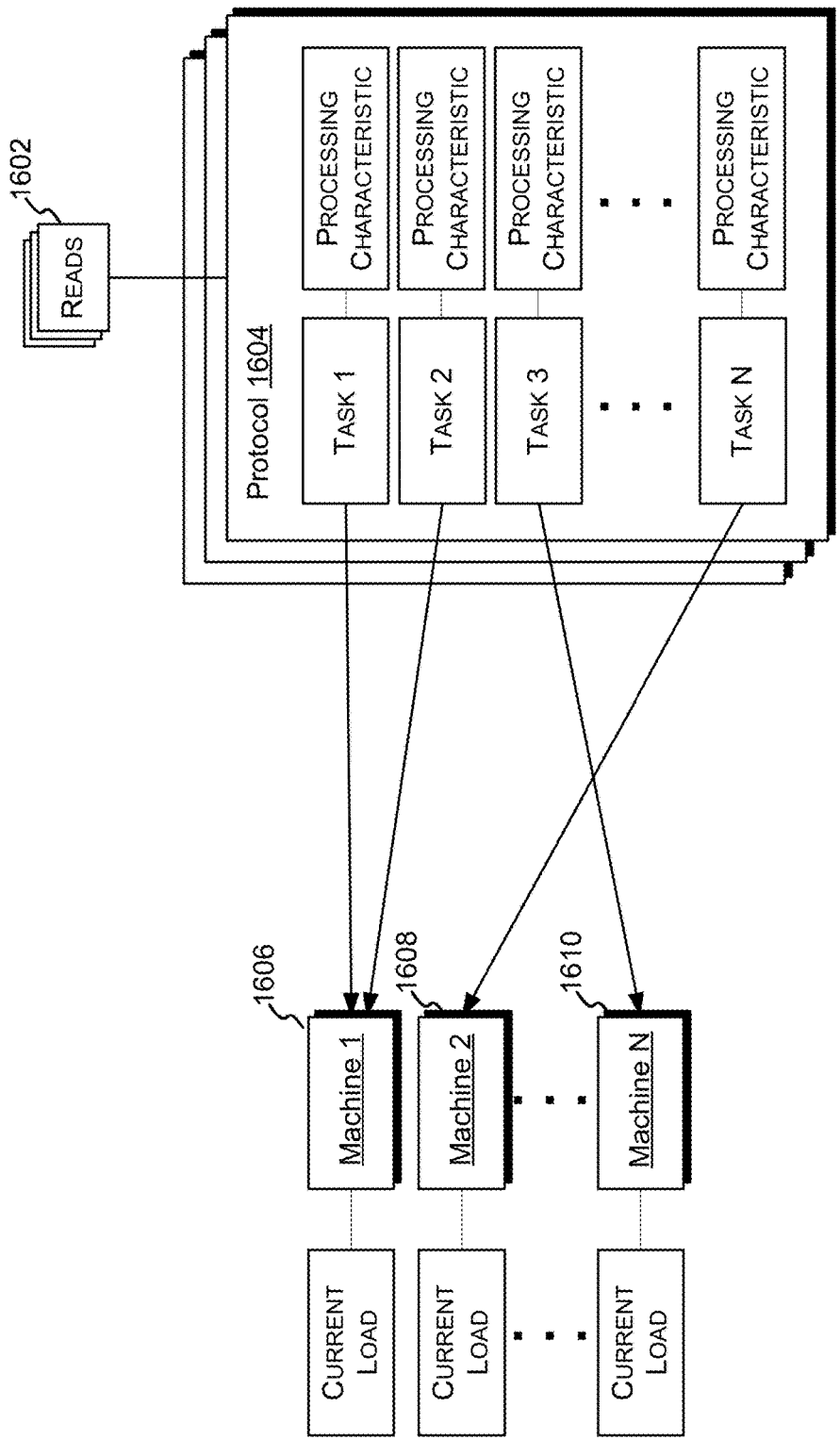
FIG. 16 illustrates an example of task-distribution to achieve load-balancing across a plurality of machines in accordance with embodiments of the present disclosure.

FIG. 16 illustrates an example of task-distribution to achieve load-balancing across a plurality of machines in accordance with embodiments of the present disclosure.

In some embodiments, there may be a set of reads 1602 (e.g., a set of reads associated with a client) that is received by the assessment system. The set of reads 1602 may correspond to a single client and sample, or they may correspond to different clients or samples. The set of reads 1602 may be associated with a protocol 1604 that identifies multiple tasks in a workflow to perform processing and analysis on the set of reads 1602 (e.g., determine a state-transition likelihood). As shown in the figure, the protocol 1604 defines a first task, a second task, a third task, and so forth—up to a Nth task. Examples of the tasks were previously described in FIG. 14.

In some embodiments, the assessment system may generate a processing characteristic associated with each of the tasks defined by the protocol 1604. This processing characteristic may reflect a predicted resource expenditure and/or time profile for each task to be processed by a machine (e.g., the first machine 1606, the second machine 1608, up to the Nth machine 1610). Based on the processing characteristic associated with each task, a load-balancing scheduler (not shown, but one example could be scheduler 912 in FIG. 9) could assign tasks to the various machines to equilibrate machine loads (e.g., assign tasks in a manner that results in the first machine 1606, the second machine 1608, up to the Nth machine 1610 using similar amounts of processing, memory, computing resources, etc.). In order to do this, the assessment system may also have to consider the current load associated with each of the machines (e.g., each of the first machine 1606, the second machine 1608, and so forth may have a current load associated with it, and those loads may differ). The assessment system may take the differences in the current loads of the various machines into consideration when assigning the tasks.

As shown in the figure, the assessment system may have determined that balancing the loads among the various machines involves assigning a first task and a second task associated with a read to the first machine 1606 based on the processing characteristics associated with those tasks and the current load of the first machine 1606. The data need to perform the first and second tasks may also be provided to the first machine 1606. Similarly, the third task is assigned to the Nth machine 1610 and the Nth task is assigned to the second machine 1608.

In some embodiments, the determination of the processing characteristic associated with each task may require a pre-assessment or an initial task that is performed to evaluate subsequent tasks in the workflow. For example, the first task associated with each read of a set of reads may include an initial pair-wise alignment for that read against a reference dataset in order to determine whether there is a perfect match, no match, or multiple matches to portions of the reference dataset. This first task for each read may be distributed among one or more of the machines in order to assess the processing characteristic associated with any subsequent alignment tasks. For instance, an alignment task may have a processing characteristic that is dependent on how many potential alignment sites there may be for a read. In some embodiments, an alignment task may be sub-divided based on a number of potential alignment sites. In some embodiments, the tasks of the workflow defined by the protocol 1604 may be modified or redefined such that the tasks have similar processing characteristics before those tasks are distributed among the various machines. In some embodiments, the tasks of the workflow defined by the protocol may be divided among the various machines based on number of the tasks. Thus, one way of load-balancing is to provide an even quantity of tasks to each machine with each task having similar processing characteristics. This may reduce the need for a cluster management system.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium", "storage" or "memory" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A computer-implemented method comprising:
   receiving a plurality of reads, each read of the plurality of reads being associated with a client;
   performing, for each read of the plurality of reads, an alignment process using the read and a reference data set to generate an alignment result, the alignment result identifying one or more portions of the reference data set to which the read is to be aligned, the reference data set including, at each position of a plurality of positions, a reference-data identifier corresponding to the position;
   identifying a first pre-identified portion of the reference data set, the first pre-identified portion being related to a second pre-identified portion of the reference data set, and each of the first pre-identified portion and the second pre-identified portion corresponding to a subset of the plurality of positions;
   for each position of one or more positions of the first pre-identified portion:
      identifying a subset of the plurality of reads, each read in the subset having an identifier aligned to the position;
      for each of one or more identifiers:
         determining a quantity of the subset of reads that include the identifier at a read position aligned to the position;
         determining that a downstream-processing criterion is satisfied based on the quantity;
         in response to determining that the downstream-processing criterion is satisfied:
            determining that the identifier matches a reference-data identifier in the reference data set at the position; and
            in response to determining that the identifier does not match a reference-data identifier at the reference data set at the position:
               defining a sparse indicator that represents a difference between the identifier and the reference-data identifier; and
               assigning the sparse indicator to a bucket representative of a state-transition likelihood attributable to the sparse indicator;
   determining that a data verification condition is satisfied based on the bucket assignments; and
   in response to determining that the data verification condition is satisfied, transmitting a communication to a data generation system that identifies the client.

2. The computer-implemented method of claim 1, wherein, for each read of at least one read of the plurality of reads, performing the alignment process includes:
   identifying, for each portion of a plurality of portions of the reference data set, an alignment score that represents a degree of correspondence between the read and the portion;
   identifying one or more alignment scores that are above a relative or absolute threshold;
   determining that an alignment score of the one or more alignment scores is associated with the first pre-identified portion or the second pre-identified portion;
   upon determining that an alignment score of the one or more alignments scores is associated with the first pre-identified portion or the second pre-identified portion, defining the one or more portions to include a first portion corresponding to at least part of the first pre-identified portion and a second portion corresponding to at least part of the second pre-identified portion.

3. The computer-implemented method of claim 1, further comprising, for each position of one or more positions of the first pre-identified portion and for each of one or more identifiers:
   defining a representation metric for the position to be the quantity divided by a number of reads in the subset, wherein the downstream-processing criterion is configured to be satisfied when the representation metric exceeds a threshold.

4. The computer-implemented method of claim 1, further comprising:
   receiving, from the data generation system, a second communication that includes one or more verified reads;
   performing, for each read of the one or more verified reads, an alignment process using the read and a reference data set to generate an alignment result, the alignment result identifying a of the reference data set to which the read is to be aligned;
   for each position of one or more positions of the portion of the reference data set:
      determining a client-data identifier to be associated with the position based on an identifier in the read that is aligned to the position;
      determining that the client-data identifier matches a reference-data identifier in the reference data set at the position; and
      in response to determining that the client-data identifier does not match a reference-data identifier at the reference data set at the position:
         defining a verified sparse indicator that represents a difference between the client-data identifier and the reference-data identifier;
         generating a state-transition likelihood based on the verified sparse indicators; and
         outputting the state-transition likelihood in association with an identifier of the client.

5. The computer-implemented method of claim 1, wherein determining that the data verification condition is satisfied includes determining, for each defined sparse indicator, whether the data verification condition is satisfied based on a bucket assignment associated with the sparse indicator.

6. The computer-implemented method of claim 1, wherein the data verification condition is configured to be satisfied when a quantity of sparse indicators assigned to any of one or more particular buckets exceeds a threshold.

7. The computer-implemented method of claim 1, wherein each of the plurality of reads includes a read generated by processing a sample associated with the client, the processing being of a first type, and wherein the communication corresponds to a request to perform a processing of a second type.

8. The computer-implemented method of claim 1, wherein the plurality of reads is received from the data generation system.

9. A system comprising:
one or more data processors; and
a non-transitory computer readable storage medium containing instructions which when executed on the one or more data processors, cause the one or more data processors to perform actions including:
receiving a plurality of reads, each read of the plurality of reads being associated with a client;
performing, for each read of the plurality of reads, an alignment process using the read and a reference data set to generate an alignment result, the alignment result identifying one or more portions of the reference data set to which the read is to be aligned, the reference data set including, at each position of a plurality of positions, a reference-data identifier corresponding to the position;
identifying a first pre-identified portion of the reference data set, the first pre-identified portion being related to a second pre-identified portion of the reference data set, and each of the first pre-identified portion and the second pre-identified portion corresponding to a subset of the plurality of positions;
for each position of one or more positions of the first pre-identified portion:
identifying a subset of the plurality of reads, each read in the subset having an identifier aligned to the position;
for each of one or more identifiers:
determining a quantity of the subset of reads that include the identifier at a read position aligned to the position;
determining that a downstream-processing criterion is satisfied based on the quantity;
in response to determining that the downstream-processing criterion is satisfied:
determining that the identifier matches a reference-data identifier in the reference data set at the position; and
in response to determining that the identifier does not match a reference-data identifier at the reference data set at the position:
defining a sparse indicator that represents a difference between the identifier and the reference-data identifier; and
assigning the sparse indicator to a bucket representative of a state-transition likelihood attributable to the sparse indicator;
determining that a data verification condition is satisfied based on the bucket assignments; and
in response to determining that the data verification condition is satisfied, transmitting a communication to a data generation system that identifies the client.

10. The system of claim 9, wherein, for each read of at least one read of the plurality of reads, performing the alignment process includes:
identifying, for each portion of a plurality of portions of the reference data set, an alignment score that represents a degree of correspondence between the read and the portion;
identifying one or more alignment scores that are above a relative or absolute threshold;
determining that an alignment score of the one or more alignment scores is associated with the first pre-identified portion or the second pre-identified portion; and
upon determining that an alignment score of the one or more alignments scores is associated with the first pre-identified portion or the second pre-identified portion, defining the one or more portions to include a first portion corresponding to at least part of the first pre-identified portion and a second portion corresponding to at least part of the second pre-identified portion.

11. The system of claim 9, wherein the actions further include, for each position of one or more positions of the first pre-identified portion and for each of one or more identifiers:
defining a representation metric for the position to be the quantity divided by a number of reads in the subset, wherein the downstream-processing criterion is configured to be satisfied when the representation metric exceeds a threshold.

12. The system of claim 9, wherein the actions further include:
receiving, from the data generation system, a second communication that includes one or more verified reads;
performing, for each read of the one or more verified reads, an alignment process using the read and a reference data set to generate an alignment result, the alignment result identifying a of the reference data set to which the read is to be aligned;
for each position of one or more positions of the portion of the reference data set:
determining a client-data identifier to be associated with the position based on an identifier in the read that is aligned to the position;
determining that the client-data identifier matches a reference-data identifier in the reference data set at the position; and
in response to determining that the client-data identifier does not match a reference-data identifier at the reference data set at the position:
defining a verified sparse indicator that represents a difference between the client-data identifier and the reference-data identifier;
generating a state-transition likelihood based on the verified sparse indicators; and
outputting the state-transition likelihood in association with an identifier of the client.

13. The system of claim 9, wherein determining that the data verification condition is satisfied includes determining, for each defined sparse indicator, whether the data verification condition is satisfied based on a bucket assignment associated with the sparse indicator.

14. The system of claim 9, wherein the data verification condition is configured to be satisfied when a quantity of sparse indicators assigned to any of one or more particular buckets exceeds a threshold.

15. The system of claim 9, wherein each of the plurality of reads includes a read generated by processing a sample associated with the client, the processing being of a first type, and wherein the communication corresponds to a request to perform a processing of a second type.

16. The system of claim 9, wherein the plurality of reads is received from the data generation system.

17. A computer-program product tangibly embodied in a non-transitory machine-readable storage medium, including instructions configured to cause one or more data processors to perform actions including:
receiving a plurality of reads, each read of the plurality of reads being associated with a client;
performing, for each read of the plurality of reads, an alignment process using the read and a reference data set to generate an alignment result, the alignment result identifying one or more portions of the reference data set to which the read is to be aligned, the reference data set including, at each position of a plurality of positions, a reference-data identifier corresponding to the position;
identifying a first pre-identified portion of the reference data set, the first pre-identified portion being related to a second pre-identified portion of the reference data set, and each of the first pre-identified portion and the second pre-identified portion corresponding to a subset of the plurality of positions;
for each position of one or more positions of the first pre-identified portion:
identifying a subset of the plurality of reads, each read in the subset having an identifier aligned to the position;
for each of one or more identifiers:
determining a quantity of the subset of reads that include the identifier at a read position aligned to the position;
determining that a downstream-processing criterion is satisfied based on the quantity;
in response to determining that the downstream-processing criterion is satisfied:
determining that the identifier matches a reference-data identifier in the reference data set at the position; and
in response to determining that the identifier does not match a reference-data identifier at the reference data set at the position:
defining a sparse indicator that represents a difference between the identifier and the reference-data identifier; and
assigning the sparse indicator to a bucket representative of a state-transition likelihood attributable to the sparse indicator;
determining that a data verification condition is satisfied based on the bucket assignments; and
in response to determining that the data verification condition is satisfied, transmitting a communication to a data generation system that identifies the client.

18. The computer-program product of claim 17, wherein, for each read of at least one read of the plurality of reads, performing the alignment process includes:
identifying, for each portion of a plurality of portions of the reference data set, an alignment score that represents a degree of correspondence between the read and the portion;
identifying one or more alignment scores that are above a relative or absolute threshold;
determining that an alignment score of the one or more alignment scores is associated with the first pre-identified portion or the second pre-identified portion; and
upon determining that an alignment score of the one or more alignments scores is associated with the first pre-identified portion or the second pre-identified portion, defining the one or more portions to include a first portion corresponding to at least part of the first pre-identified portion and a second portion corresponding to at least part of the second pre-identified portion.

19. The computer-program product of claim 17, wherein the actions further include, for each position of one or more positions of the first pre-identified portion and for each of one or more identifiers:
defining a representation metric for the position to be the quantity divided by a number of reads in the subset, wherein the downstream-processing criterion is configured to be satisfied when the representation metric exceeds a threshold.

20. The computer-program product of claim 17, wherein the actions further include:
receiving, from the data generation system, a second communication that includes one or more verified reads;
performing, for each read of the one or more verified reads, an alignment process using the read and a reference data set to generate an alignment result, the alignment result identifying a of the reference data set to which the read is to be aligned;
for each position of one or more positions of the portion of the reference data set:
determining a client-data identifier to be associated with the position based on an identifier in the read that is aligned to the position;
determining that the client-data identifier matches a reference-data identifier in the reference data set at the position; and
in response to determining that the client-data identifier does not match a reference-data identifier at the reference data set at the position:
defining a verified sparse indicator that represents a difference between the client-data identifier and the reference-data identifier;
generating a state-transition likelihood based on the verified sparse indicators; and
outputting the state-transition likelihood in association with an identifier of the client.

\* \* \* \* \*